(12) United States Patent
McKirdy

(10) Patent No.: US 11,664,123 B2
(45) Date of Patent: May 30, 2023

(54) BARCODE GENERATION AND IMPLEMENTATION METHOD AND SYSTEM FOR PROCESSING INFORMATION

(71) Applicant: Sean McKirdy, Newington, CT (US)

(72) Inventor: Sean McKirdy, Newington, CT (US)

(*) Notice: Subject to any disclaimer, the term of this patent is extended or adjusted under 35 U.S.C. 154(b) by 0 days.

(21) Appl. No.: 17/181,423

(22) Filed: Feb. 22, 2021

(65) Prior Publication Data

US 2021/0350923 A1    Nov. 11, 2021

Related U.S. Application Data

(63) Continuation of application No. 16/412,585, filed on May 15, 2019, now Pat. No. 10,926,135.

(51) Int. Cl.

| | | |
|---|---|---|
| *A63B 24/00* | (2006.01) | |
| *G06K 7/14* | (2006.01) | |
| *G06K 19/06* | (2006.01) | |
| *G06K 19/07* | (2006.01) | |
| *G16H 40/67* | (2018.01) | |
| *G06Q 30/02* | (2012.01) | |
| *A61B 5/0205* | (2006.01) | |
| *G16H 20/30* | (2018.01) | |
| *G06Q 30/0251* | (2023.01) | |
| *G16H 40/63* | (2018.01) | |
| *G16H 20/60* | (2018.01) | |
| *A61B 5/021* | (2006.01) | |
| *A61B 5/024* | (2006.01) | |
| *A61B 5/00* | (2006.01) | |

(52) U.S. Cl.
CPC ........... *G16H 40/67* (2018.01); *A61B 5/0205* (2013.01); *A63B 24/0062* (2013.01); *G06K 7/1413* (2013.01); *G06K 19/06028* (2013.01); *G06K 19/06112* (2013.01); *G06K 19/0718* (2013.01); *G06Q 30/0271* (2013.01); *G16H 20/30* (2018.01); *A61B 5/021* (2013.01); *A61B 5/024* (2013.01); *A61B 5/4872* (2013.01); *A63B 2230/01* (2013.01); *A63B 2230/06* (2013.01); *A63B 2230/30* (2013.01); *A63B 2230/70* (2013.01); *G16H 20/60* (2018.01); *G16H 40/63* (2018.01)

(58) Field of Classification Search
None
See application file for complete search history.

(56) References Cited

U.S. PATENT DOCUMENTS

| | | |
|---|---|---|
| 5,890,997 A | 4/1999 | Roth |
| 6,338,433 B1 | 1/2002 | Drexler |

(Continued)

OTHER PUBLICATIONS

U.S. Appl. No. 10/417,103, filed Nov. 13, 2003, Patrick J. Capuano.

(Continued)

*Primary Examiner* — Kristy A Haupt

(57) ABSTRACT

A system and method for generating and implementing a barcode is provided, wherein the system includes a data generation device configured to receive data and generate barcode data response to the received data, a barcode generation device, configured to receive the barcode data and generate a barcode responsive to the received barcode data, a display device, configured to display the barcode and a barcode receiving device, configured to receive the barcode and operate in response to the barcode.

20 Claims, 11 Drawing Sheets

(56) References Cited

U.S. PATENT DOCUMENTS

| | | |
|---|---|---|
| 6,514,199 B1 | 2/2003 | Alessandri |
| 6,568,596 B1 | 5/2003 | Shaw |
| 7,056,265 B1 | 6/2006 | Shea |
| 7,434,724 B2 | 6/2008 | Lane |
| 7,578,432 B2 | 8/2009 | Libin et al. |
| 7,628,318 B2 | 12/2009 | Melick et al. |
| 7,810,720 B2 | 10/2010 | Lovett |
| 7,909,741 B2 | 3/2011 | Kim et al. |
| 7,914,419 B2 | 3/2011 | Karkanias et al. |
| 7,934,641 B2 | 5/2011 | Melick et al. |
| 7,942,328 B2 | 5/2011 | Snyder et al. |
| 7,988,037 B2 | 5/2011 | Yach |
| 7,988,050 B2 | 8/2011 | Kitada et al. |
| 8,131,478 B2 | 3/2012 | Kai |
| 2008/0032864 A1* | 2/2008 | Hakki ............... A63B 71/0622 482/8 |
| 2008/0300109 A1* | 12/2008 | Karkanias .......... A63B 24/0087 482/8 |
| 2011/0210170 A1* | 9/2011 | Arguello ............ H04M 17/00 235/380 |

OTHER PUBLICATIONS

U.S. Appl. No. 10/617,525, filed Jan. 13, 2005, Chen et al..
U.S. Appl. No. 11/015,635, filed Jul. 14, 2005, Meiick et al..
U.S. Appl. No. 11/089,241, filed Sep. 28, 2006, Kondrat et al.
U.S. Appl. No. 11/247,430, filed Feb. 8, 2007, Rao et al.
U.S. Appl. No. 11/754,565, filed Dec. 4, 2008, Karkanias et al..
U.S. Appl. No. 12/778,067, filed Sep. 2, 2010, Michael J. Shea.
U.S. Appl. No. 12/469,222, filed Nov. 25, 2010, McCombie et al.
U.S. Appl. No. 12/546,152, filed Feb. 24, 2011, Richard Wojdyla.
U.S. Appl. No. 12/752,348, filed Mar. 10, 2011, Frysz et al.
U.S. Appl. No. 12/879,932, filed Mar. 17, 2011, Gagner et al.
U.S. Appl. No. 12/572,386, filed Apr. 7, 2011, Brown et al.
U.S. Appl. No. 12/907,672, filed Apr. 21, 2011, Otavio Good.
U.S. Appl. No. 12/610,445, filed May 5, 2011, David Paul Yach.
U.S. Appl. No. 12/953,868, filed Jun. 30, 2011, Bower et al.
U.S. Appl. No. 11/247,416, filed Feb. 8, 2007, Rao et al.
U.S. Appl. No. 12/238,994, filed Apr. 1, 2010, Glenn Patton Bradford.

\* cited by examiner

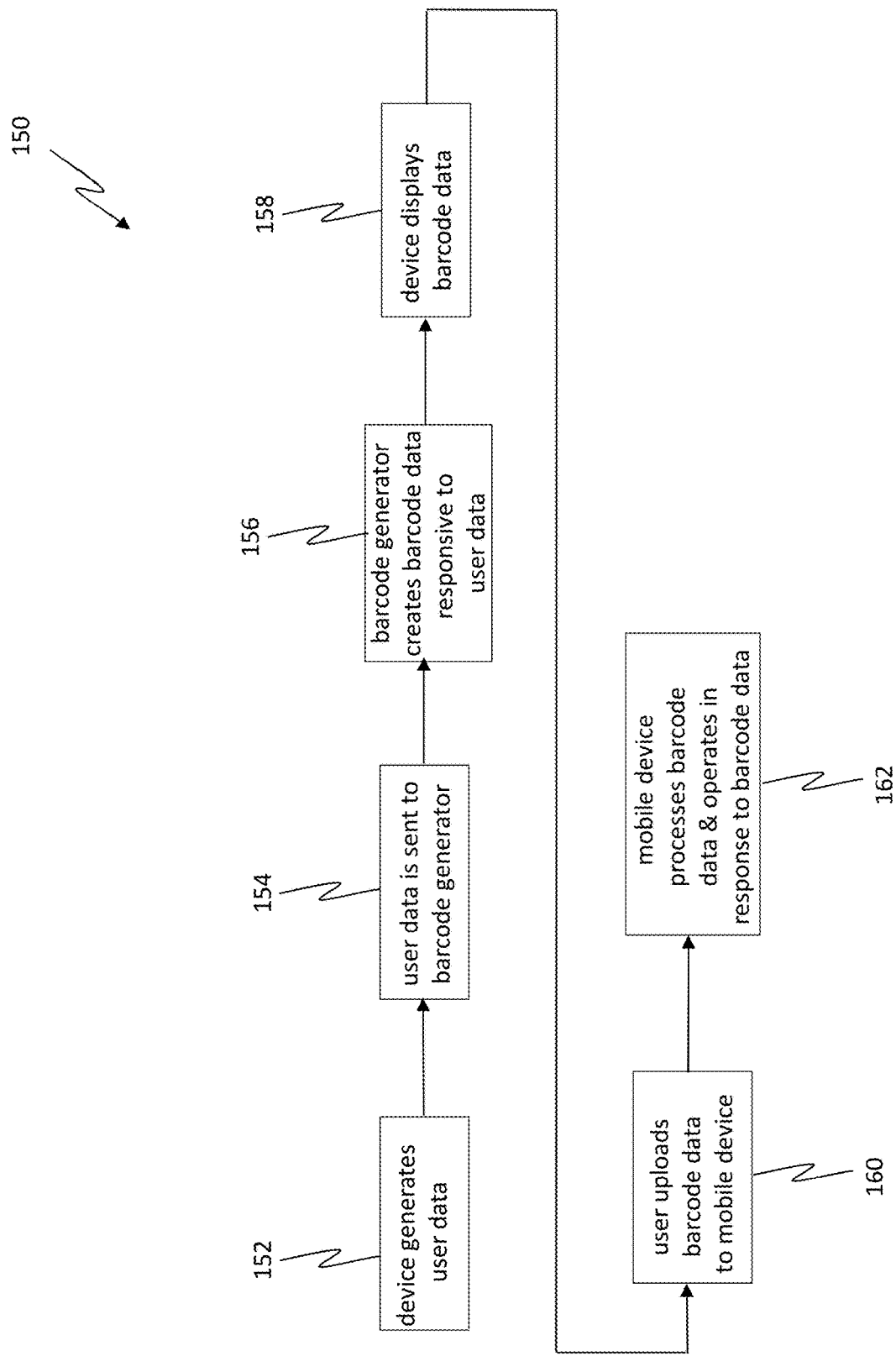

BARCODE GENERATION AND IMPLEMENTATION METHOD AND SYSTEM FOR PROCESSING INFORMATION

CROSS-REFERENCE TO RELATED PATENT APPLICATIONS

The present application is a continuation application of U.S. Non-Provisional patent application Ser. No. 16/412,585, entitled "Barcode Generation and Implementation Method and System for Processing Information," filed May 15, 2019 and claims the benefit of priority of U.S. Non-Provisional patent application Ser. No. 16/412,585 which claims the benefit of U.S. Non-Provisional patent application Ser. No. 15/175,599, entitled "Barcode Generation and Implementation Method and System for Processing Information," filed Jun. 6, 2016 which claims the benefit of priority of U.S. patent application Ser. No. 13/567,337, entitled "Barcode Generation and Implementation Method and System for Processing Information," filed Aug. 6, 2012 which claims benefit of U.S. Provisional Patent Application Ser. No. 61/515,728, entitled "System and Method for Processing Information," filed Aug. 5, 2011, U.S. Provisional Patent Application Ser. No. 61/539,587, entitled "System and Method for Processing Information," filed Sep. 27, 2011 and U.S. Provisional Patent Application Ser. No. 61/622,175, entitled "System and Method for Processing Information," filed Apr. 10, 2012, the contents of all of which are incorporated herein by reference in their entireties.

FIELD OF THE INVENTION

This disclosure relates generally to the processing of information and more particularly to a system and method for obtaining, processing and implementing information, such as exercise, health and gaming related information.

BACKGROUND OF THE INVENTION

For many years, people have recognized the health benefits of exercising on a regular basis. As a result, a whole industry dedicated to physical fitness and exercise was created and has grown into a multi-billion dollar a year industry. Areas of this industry, which includes personal trainers, fitness clubs, nutrition based products, exercise gear and fitness competitions, tend to complement each other and work hand in hand with each other to help individuals achieve an effective physical fitness regimen. For example, a large number of fitness clubs employ nutritionists and personal trainers that are readily available to advise their fitness club members, wherein the basic services that these personal trainers perform are primarily three fold. First, the trainers develop an exercise regime tailored to individual clients and advise their clients on how to safely and effectively exercise. Second, the trainers track the exercise performance of the client over the duration of the training period and analyze the client's exercise performance data to identify where the client is or is not showing improvements. The trainer may then adjust the exercise regime of the client to maximize the benefit to the client. Third, the trainer provides motivation to their client, which ultimately helps the client to maintain their exercise regime. This not only aids the client in maintaining a healthy lifestyle, but also helps the fitness club retain their membership.

As mobile technology becomes more sophisticated and prevalent in the general population, applications that are specific to the health and fitness industry are being developed on a broader basis to help trainers and individuals track and process (such as information validation) the information related to their (or their clients) habits and exercise regimes. For example, as the "smart-phone" market has exploded in popularity, solutions that focus on using the smart-phone as the focal point for collecting and viewing health related information are becoming more readily available. In fact, there are systems currently available that allow a user to physically plug their mobile device into an exercise machine, such as a treadmill, to capture data generated in response to their workout. This date can then be viewed directly on the mobile device or uploaded through a cellular network to a website, where the data can be processed further and/or viewed at a later time.

Unfortunately, in spite of the popularity and sophistication of these devices several major hurdles prevent or discourage the use of these applications. Firstly, as there are no standards for these devices relative to exercise machines not all makes and models of fitness equipment have the capability installed to support data communication with the a mobile phone or device. Secondly, this is also true for the mobile phone or device. Because there are no standards (as mentioned above) and there are many different types of mobile phone or devices available, each of which have their own proprietary communication protocols and operating systems, it is near impossible for fitness equipment manufacturers to be able to provide a universal 'plug in' solution that operates with all of the mobile phones or devices available.

Thirdly, there are also exercise tracking systems that require physical data lines to be connected to every exercise machine in order to facilitate the communications between the machine and a master server located inside the fitness facility. This approach is not only costly in that it requires the purchase and installation of upfront capital equipment, but it also requires the maintenance and repair of physical data lines that are in high foot traffic areas near the machines. Although, these systems might be able to employ a wireless data solution, the initial purchase and installation cost along with recurring maintenance cost is still substantial.

Fourthly, machines or electronic devices (exercise and non-exercise related machines) that require a person to interface with the machine/device by traditional touch actions (i.e. member buttons or touch screen interface displays) can often be susceptible to the machine interface failing for numerous reasons.

SUMMARY OF THE INVENTION

A system for generating and implementing a barcode is provided, wherein the system includes a data generation device configured to receive data and generate barcode data response to the received data, a barcode generation device, configured to receive the barcode data and generate a barcode responsive to the received barcode data, a display device, configured to display the barcode and a barcode receiving device, configured to receive the barcode and operate in response to the barcode.

A method for generating and implementing a barcode is provided and includes generating barcode data via a data generation device, sending the barcode data to a barcode generator, creating the barcode responsive to the barcode data, displaying the barcode, uploading the barcode into a mobile device and processing the barcode responsive to the barcode data.

BRIEF DESCRIPTION OF DRAWINGS

The foregoing and other features and advantages of the present invention will be better understood from the following detailed description of illustrative embodiments, taken in conjunction with the accompanying drawings in which:

FIG. 1B is a high level operational block diagram illustrating a method for obtaining, communicating and processing information via a barcode process, in accordance with one embodiment of the present invention.

DETAILED DESCRIPTION OF THE INVENTION

Figure 1A:
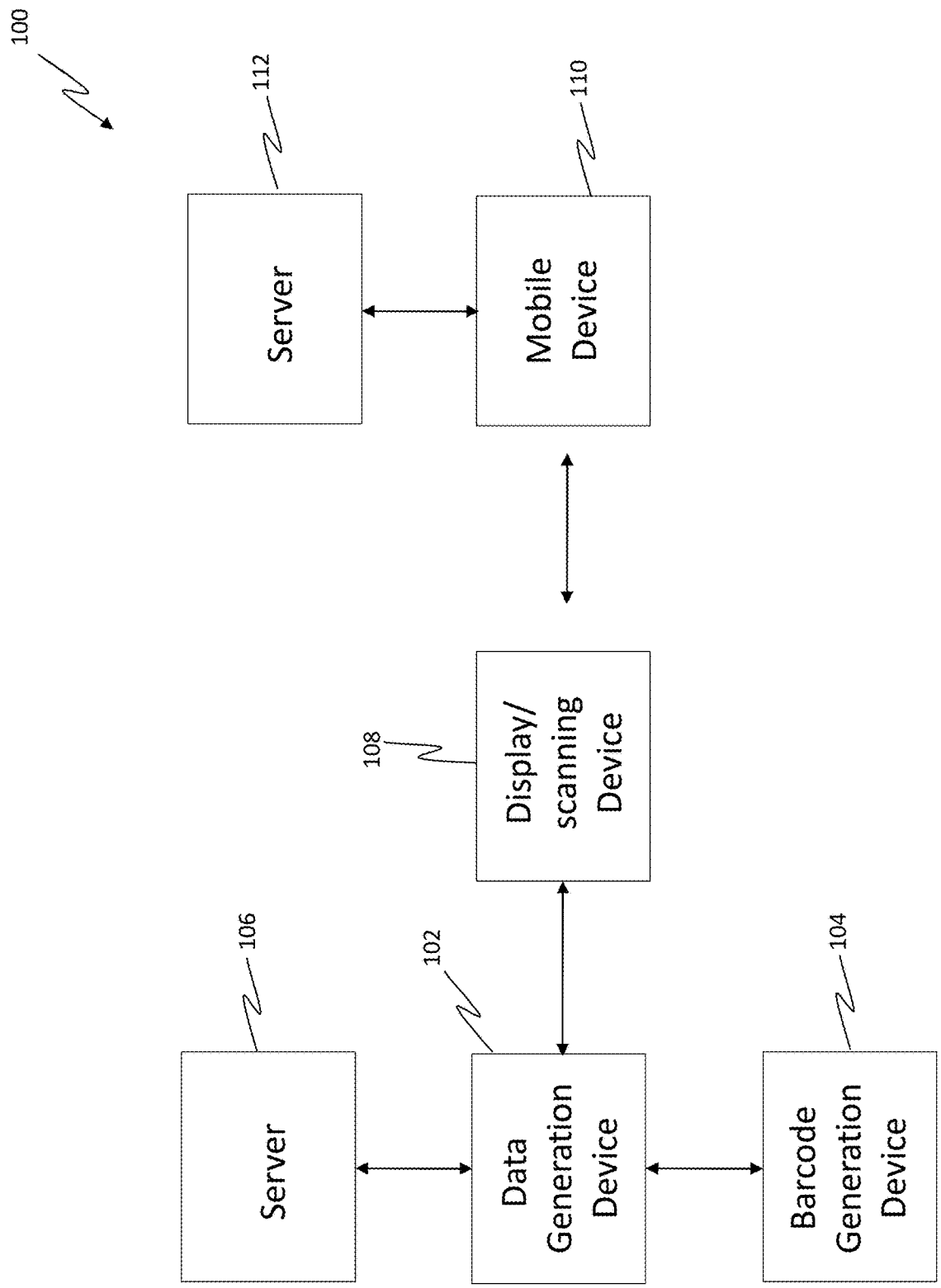
FIG. 1A is a system schematic block diagram illustrating a general overall system for obtaining, communicating and processing information via a barcode process, in accordance with one embodiment of the present invention

Referring to FIG. 1A, as discussed further hereinafter, an overall system schematic block diagram illustrating a general system 100 for obtaining, communicating and processing information via a barcode is shown and includes a data generation device 102 that is in signal communication with a barcode generation device 104 and (optionally) a server 106. The data generation device 102 is also associated with a display (and/or printer) device 108 for displaying the barcode that is generated. A mobile device 110 is provided for scanning the generated barcode via the display device 108 and the mobile device 110 may or may not be associated with a server 112.

Referring to FIG. 1B, an operational block diagram illustrating a method 150 for obtaining, communicating and processing information via a barcode process is shown, in accordance with one embodiment of the present invention. As shown, the method 100 includes generating user data via a device (such as an exercise device, a glucometer, a pedometer, etc.) as shown in operational block 152. The user data is then sent to a barcode generator, as shown in operational block 154, where the barcode generator may be integrated into the device generating the data or the barcode generator may be a separate device. The barcode generator then processes the user data (as discussed further herein below) and generates barcode data, as shown in operational block 156. It should be appreciated that the barcode data may be in graphical form (i.e. a barcode) or the barcode data may be in data form where a separate device can generate the graphical barcode (such as a printer or a device with a display screen). The barcode data may then be displayed in graphical form via a display screen (or via a physical printout), as shown in operational block 158. A user may then upload the barcode data by scanning the barcode with their mobile device, as shown in operational block 160, where the mobile device processes the barcode data and if necessary, operates in response to the barcode data, as shown in operational block 162.

Figure 2:
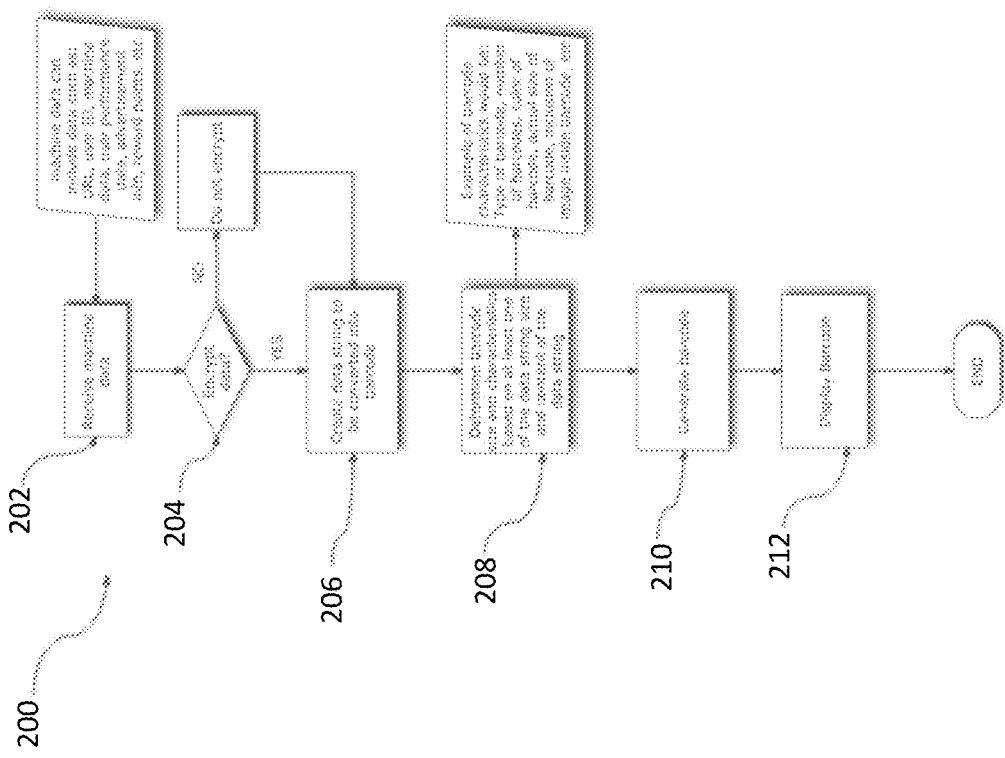
FIG. 2 is an operational block diagram illustrating a method for generating a barcode, in accordance with one embodiment of the present invention.

Referring to FIG. 2, an operational block diagram illustrating a method 200 for generating a barcode is shown, in accordance with one embodiment of the present invention. As shown, the method 200 includes receiving user data, as shown in operational block 202, where user data may include data related to the field of the device as discussed hereinafter. For example, the user data may include hyperlink information (i.e. Universal Resource Locator data), device data, user performance data, user biological data, advertisement data, channel viewing data, etc. The method may include determining whether to encrypt the user data, as shown in operational block 204, however, it should be appreciated that this operation may be optional as desired. A data string is then generated using the barcode data (whether encrypted or not) as shown in operational block 206, and the amount of data in the data string is determined, as shown in operational block 208. At this point, the characteristics and size of the barcode to be generated are automatically determined responsive to the amount and type of data in the data string, and the barcode is generated responsive to the determined characteristics and size, as shown in operational block 210. The generated barcode may then be displayed, as shown in operational block 212.

Figure 3:
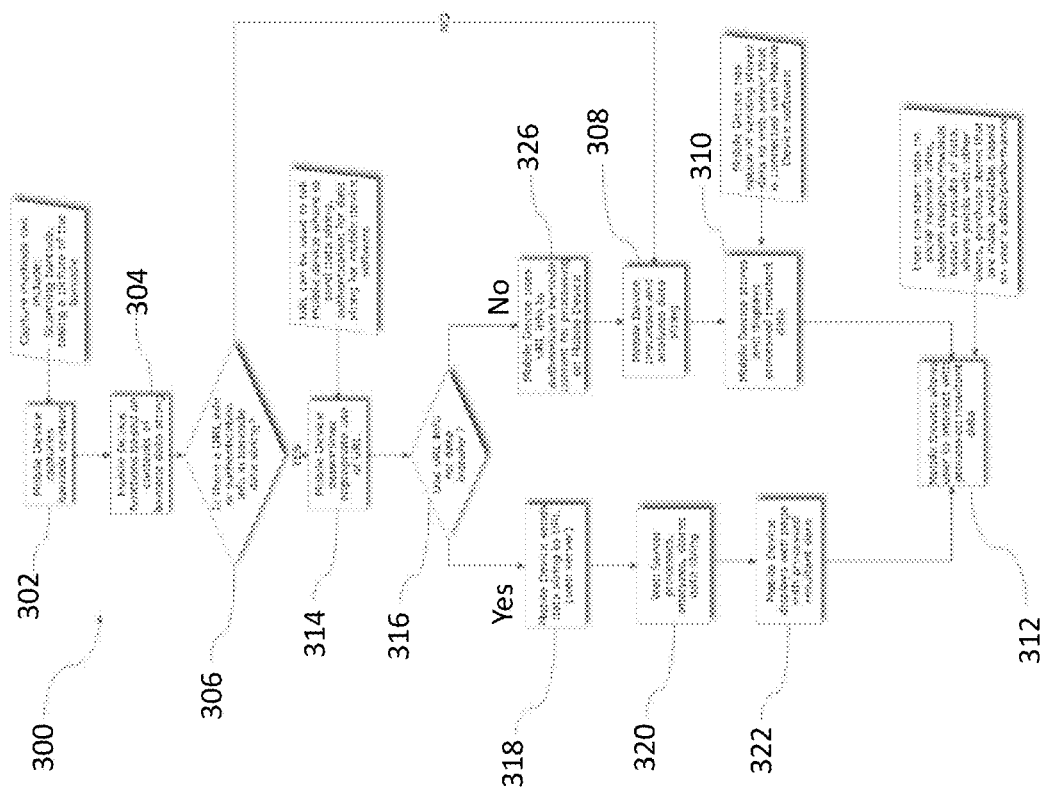
FIG. 3 is an operational block diagram illustrating a method for uploading and processing a barcode via a mobile device, in accordance with one embodiment of the present invention.

Referring to FIG. 3, an operational block diagram illustrating a method 300 for uploading and processing a barcode via a mobile device is shown, in accordance with one embodiment of the present invention. The method 300 includes uploading the barcode data into a mobile device, as shown in operational block 302, where this may be accomplished by activating the scanning software on the mobile device and exposing the barcode to the camera such that the scanning software can view and receive the image of the barcode. When the image of the barcode is uploaded into the mobile device, the mobile device may operate based on the barcode data that is uploaded, as shown in operational block 304. The mobile device determines if there is any hyperlink to a web site (ie., a URL), as shown in operational block 306, where if no URL is present, then the mobile device processes and analyzes the barcode data), as shown in operational block 308. The processed barcode data is then stored and displayed, as shown in operational block 310. It should be appreciated that the barcode data may be processed based on instructions inside of the barcode data, based on instructions in the software application processing the barcode data, based on the application for which the barcode data was generated and/or a combination of all or some of these. The processed barcode data may then be made available to the user to allow the user to interact with the processed data, as shown in operational block 312.

However, if there is a URL present in the uploaded barcode data, the mobile device determines how the URL is to be used, as shown in operational block 314, and if the URL information is to be used for data transfer, as shown in operational block 316. If the URL information is to be used for data transfer, then the mobile device send the data string to the web server, as shown in operational block 318, where the web server processes the data string, as shown in operational block 320. The mobile device displays the web page with the processed data, as shown in operational block 322, and allows the user to interact with the processed data, as shown in operational block 312. If the URL information is not to be used for data transfer, then the mobile device uses the URL information to authenticate the barcode content for processing on the mobile device, as shown in operational block 326. The mobile device then processes the data string, as shown in operational block 308. The processed barcode data is then stored and displayed, as shown in operational block 310. It should be appreciated that the barcode data may be processed based on instructions inside of the barcode data, based on instructions in the software application processing the barcode data, based on the application for which the barcode data was generated and/or a combination of all or some of these. The processed barcode data may then be made available to the user to allow the user to interact with the processed data, as shown in operational block 312. As used herein, the term barcode refers to a 1D barcode, a 2D barcode, a 3D barcode, and/or an augmented reality marker/image/code.

It should be appreciated that one embodiment where the method of the invention can be applied involves includes collecting information related to an individual, an exercise device and/or an exercise routine of the individual. When the data is collected, the exercise device (or other type of equipment) may then generate a barcode responsive to the collected data and display the barcode. The barcode data may be displayed via display device (i.e. LCD, LED, etc.) or the barcode data may be printed out. It should be appreciated that the collected data may include any type of data suitable to the desired result, such as individual and/or machine performance data, machine setting/operation data, programmed regime data and/or biological data (such as heart rate, pulse rate, body fat, weight, height, pulse ox, etc.). Representing the data in a barcode format advantageously allows this data to be easily and securely collected and transfer between devices.

Accordingly, an embodiment of the present invention provides a solution whereby equipment (such as exercise or other types of equipment) may generate and display a barcode based on data relating to the performance of an individual's workout along with any other desired parameters, such as biometrics, past health data, equipment data (such as type of equipment, performance data, accuracy of equipment measurements, etc.) and/or workout regime. For example, as an individual is working out, the exercise machine (or an attachment to the exercise machine) and/or biological monitors can monitor and record machine and/or biological data as it generated during the workout. When the user is finished using the machine, a barcode generator (internal or external to the machine) receives the information that was collected and generates a barcode. The barcode generator device may be an add-on module (in communication with sensors from the machine and/or sensors attached to the person collecting data) to or it may be a feature integrated with the exercise device. This barcode may then be displayed to the user so that the user can scan the barcode using their mobile device.

At this point, the user can upload this information or go to another exercise machine and perform another exercise routine, whereby the data from the second exercise routine may be appended to (or integrated with) the first exercise routine. One way this may be accomplished is that before (or after) the user begins the exercise routine the user enters the barcode generated by the first exercise machine into the second exercise machine (such as by scanning). Once the user completes the routine on the second exercise machine, the barcode generator device on the second exercise machine generates another barcode responsive to data obtained from both exercise machines and displays this barcode to the user who can then scan the barcode into their mobile device. In an additional embodiment, the exercise device may simply generate a barcode based on the information collected during the use of the exercise device and display the barcode to the user. The user may upload the second barcode into their device and their device would append and/or integrated the second barcode with the first barcode. It accordance with the present invention, the data may be processed and displayed directly to the user via the mobile device, exercise device and/or the data may be sent (via hardwire, cellular or wireless network) to a backend system for processing and/or display.

It should be appreciated that the method of the invention may be implemented via any device (mobile or other) that has the ability to capture digital images (i.e. scan and/or take pictures). For example, in one embodiment, rather than scanning the barcode, the device could take a picture of the barcode for scanning by a device capable of scanning or processing by a software application capable of processing the barcode image to extract the data. This advantageously allows less sophisticated mobile devices that only have the basic ability to take pictures, capture and transfer data from the exercise equipment. The software application used to process the image may reside on a mobile device or some other processing device, such as for example a local computer/server or remote computer/server. Accordingly, the image can be displayed so that a device that has the ability to scan can scan in the image or it can be sent via email or text to a device that can print the barcode and/or interpret the barcode. This approach would also simplify the effort required in developing the mobile scanning software application, since this would allow all mobile devices with picture taking abilities to practice this method and thus benefit from the invention.

Still yet another embodiment involves the situation where an exercise machine (such as a cardio or strength device) may include a barcode reader that is capable of scanning a barcode, where the barcode contains information specific to an individual. In this case, the user can use their mobile device (cell/smart phone, iPod®, iPad®, digital camera, etc) to display their barcode (or the barcode may be on a physical card) to the scanner on the machine. The machine can scan and upload the barcode via the scanner, where the information can be used to create a workout regimen on the particular machine specific to the information that was scanned (uploaded) via the barcode. The barcode information might contain the overall exercise history of the individual, the threshold levels specific to that person (heart rate limits, weight limits for lifting, workout set limits for lifting, etc), information for how long the workout should last for the user, user biometric info (body weight, body fat %, etc), medical condition information (heart disease, diabetic, etc), etc. The machine might then automatically adjust itself based on the parameters provided by the barcode and/or the machine may also monitor the individual for over exertion or physical failure (i.e. heart attack, asthma attack, etc.) where machine can alert the fitness club workers or call emergency services.

In still yet another embodiment, the method may be used to capture bio-metric data from a kiosk (such as a health kiosk in a pharmacy) that is used to monitor and display a person's physical characteristics, such as body weight, pulse, blood pressure, body fat %, etc. This advantageously allows for an individual to capture, store and send private health information to a third party securely. For example, typically health kiosks must comply with strict HIPPA regulations and are thus constrained as to how personal health information is displayed (i.e. viewing angles, log in permissions, networking security, etc). However, by displaying the relevant health information to a person in barcode format, anyone viewing the barcode will not be able to decipher the barcode without a reader. Moreover, the data is secure because it is not linked to an individual and thus is anonymous in nature when generated by the kiosk. The information is not associated with a user until the user scans the barcode data into their mobile device. Once uploaded into the mobile device the mobile device will link the necessary user identification to the data (or the kiosk can print out a barcode that the user can scan into a remote computer (such as a home computer) where it will be associated to the individual). It should be appreciated that as data is uploaded into the mobile device and/or remote computer, the uploaded data may be combined/integrated with and/or appended to any additional data stored within (or communicated to) the mobile device and/or remote computer (such as prior health/exercise data and/or personal information). The mobile device and/or remote computer (or other device) may then generate a barcode that incorporates the newly added or appended data.

In still yet another embodiment, the invention may also operate with facial recognition software and/or hardware where the facial features of a person can be a part of the ID process to help with user authentication. Thus, the barcode could also include information regarding features of the person's face to correlate the face with other information. For example, an individual might start working out on an exercise machine that has the ability to detect the features of a person's face (or object). When the facial recognition of the individual happens, the data from that recognition process can be used to allow the person to use the machine (or not). In this case, the facial recognition data may send the results of the facial recognition process to a computer server that is controls the machine access (i.e. operation, power, etc). The data can also be stored and made ready for use by the barcode generation component, where this recognition data can be integrated as ID information inside the barcode data string, linking the data inside the barcode to a specific user.

It should be appreciated that the control of an exercise machine could also be affected by the facial recognition ability of the invention, where the user of a machine (such as a treadmill) would be able to turn on/off, control operation (and communication with aftermarket technologies such as a CSAFE enabled LCD Television display), and control machine user interface controls (GUI). In this example, a user would get on an exercise machine that has optical sensor technology and make an identified hand motion that would be recognized by the optical sensor, thus informing the machine to either turn on, or perhaps display an option of programs for the user to choose. The optical sensor might also have the ability to identify characteristics of the person such as height, weight, gender, age, etc. . . . where these data points could be used to automatically adjust the available programs specific to the individual user. Additionally, the user might also have something on them that can be recognized by the sensor to help in the identification or authentication process. For example, some gym chains use a proprietary RFID key FOB or barcode (that could be on a key chain or displayed on a cell phone or other mobile device) for club access. This may allow the fitness club to utilize an authentication process for usage of equipment based on payment status of the user. If the user does not have an authenticated device, the machine might be set up to not turn on. The exercise machine may be able to communicate directly with the gyms member management software system using data networking technology. This would be advantageous in also helping a gym understand exactly when a member was using the exercise machine, allowing for critical data to be made available to the management as desired. All of this data could be sent to a smart phone, USB drive, computer, tablet PC, etc using a method such as that described in U.S. Pat. No. 8,118,709, the contents of which is incorporated herein in its entirety.

Moreover, the invention contemplates a user being able to control the machine via movement, such as with pre-defined, recognized gestures. For example, a user of the exercise machine can interact with the recognition hardware/software by making hand movements and other motions to control the machine. These movements may control functions such as: speed up/down, change resistance, change program information, entering in data using a virtual keypad on the machine, change incline of the machine, control TV channels and volumes, navigate GUI menus to change the display of the machine, access of machine maintenance information of the machine, etc. Additionally, the machine/device that contains the optical sensor or other sensors might have the ability within the sensor hardware to handle all data processing of the optical sensor or other sensor devices and may be in communication with a secondary processing device that has the appropriate software to communicate with the sensors and to provides processing and further signal transmission to the exercise machine. Furthermore, the sensory hardware and the exercise device, and/or the sensory hardware and the secondary processing module, and/or the secondary processing module and the exercise machine may be communicated via at least one of a hard wired and/or wireless communication.

Additionally, it should be appreciated that optical sensory technology (XBOX KINECT for example) may be able to define a 'zone' (i.e. such as the footprint of the exercise machine itself) for the user which will allow the system to maintain a high degree of reliability with the ability to 'filter' out noise or external movements (such as by people passing by) that might occur outside the working 'zone' of the optical sensory technology. This advantageously allows a fitness center to place exercise machines in close proximity as each machine will require the optical sensors to only monitor the defined zone for the corresponding exercise machine. Since this invention describes the ability for the optical sensor hardware to create a defined working zone, any movements or actions that occur outside of the defined working zone will be ignored by the system or sensors.

Figure 4:
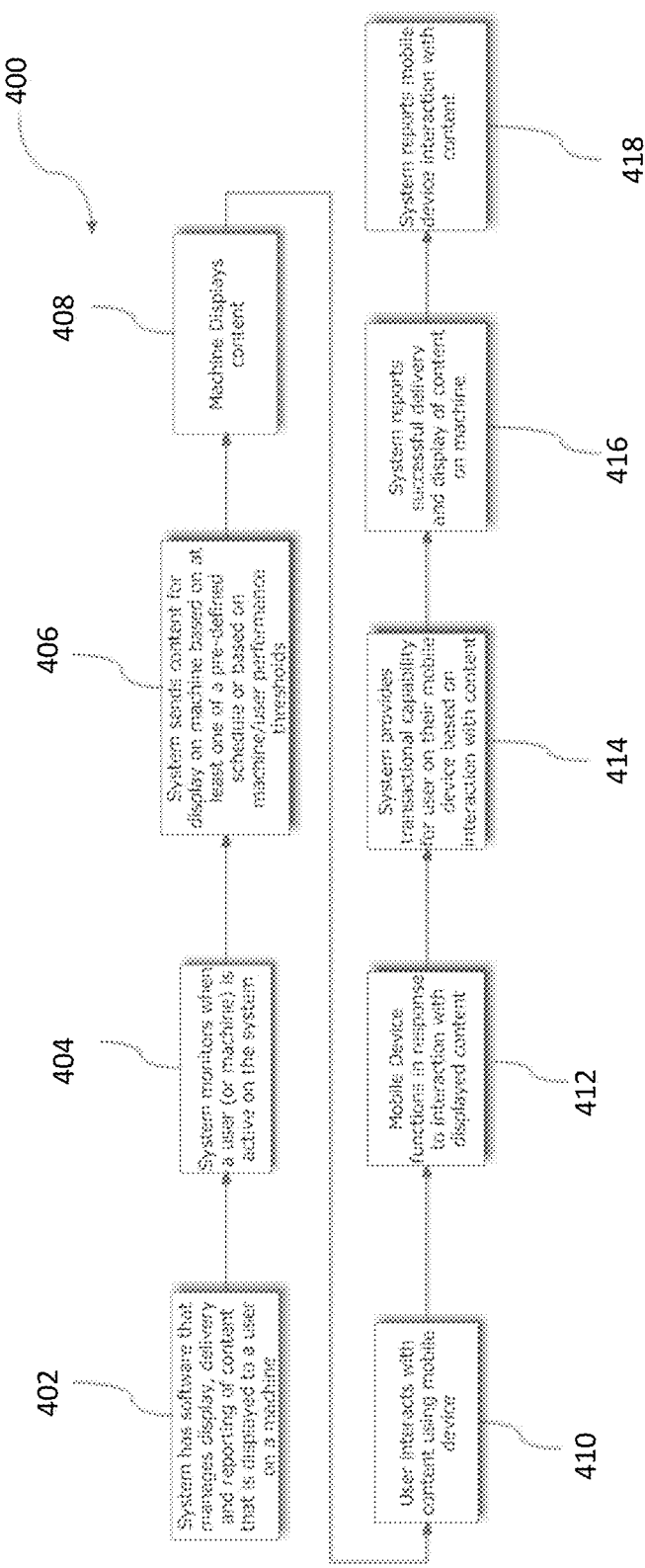
FIG. 4 is an operational block diagram illustrating a general overall method for managing the content display is shown and includes monitoring the display, delivery and/or reporting of the content that is being displayed, in accordance with one embodiment of the invention.
Figure 5:
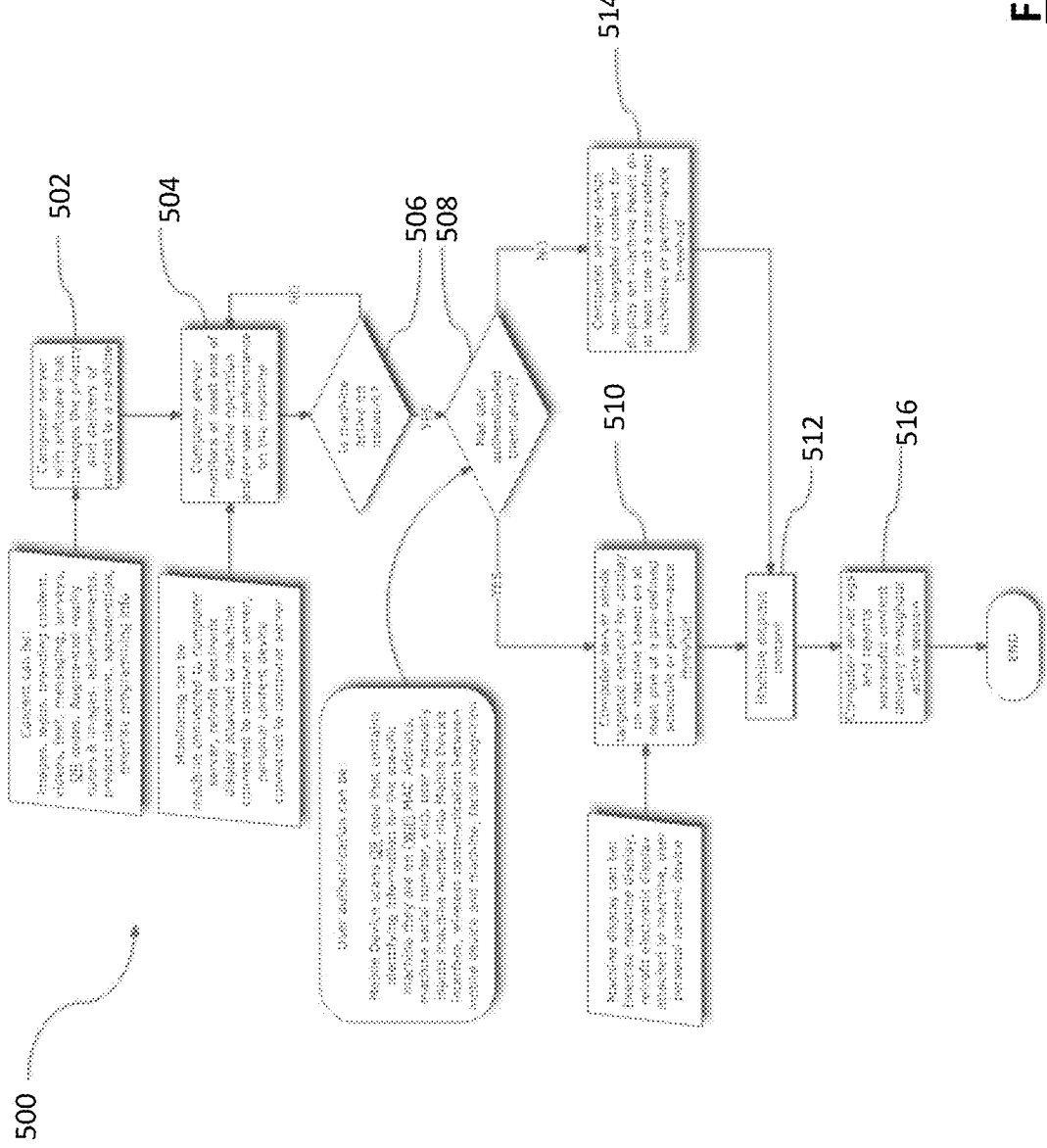
FIG. 5 is a operational block diagram illustrating a general overall method for delivering, monitoring and reporting the content being displayed is shown and includes managing priority and delivery of the content delivered to the machine, in accordance with one embodiment of the present invention.

One embodiment of this is illustrated in FIG. 4 and FIG. 5. Referring to FIG. 4, an overall general method 400 for managing the content display is shown and includes monitoring the display, delivery and/or reporting of the content that is being displayed, as shown in operational block 402. The system monitors when a user is active on the system, as shown in operational block 404, and sends content to the display for display to the user, as shown in operational blocks 406 and 408. The user may then interact with the content using a mobile device, as shown in operational block 410, and the mobile device may function in response to the user interaction, as shown in operational block 412. The system may provide the ability to conduct transactions, as shown in operational block 414, and reports the successful delivery and display of content, as shown in operational block 416. The system may also report the interaction between the mobile device and the content, as shown in operational block 418.

Referring to FIG. 5, an overall general method 500 for delivering, monitoring and reporting the content being displayed is shown and includes managing priority and delivery of the content delivered to the machine, as shown in operational block 502, and the operation of the machine and or performance of a user is monitored, as shown in operational block 504. The system then determines if the machine is on an active network, as shown in operational blocks 506, and if so, the machine determines if the user has authenticated themselves, as shown in operational block 508. If not, the operation of the machine and or performance of a user is monitored, as shown in operational block 504. If the user has authenticated themselves, then content that is targeted for display is sent for display, as shown in operational block 510, and the machine displays the content, as shown in operational block 512. If the user has not authenticated themselves, then content that has not been targeted for display is sent for display, as shown in operational block 514, and the machine displays the non-targeted content, as shown in operational block 512. The successful delivery of content is then logged and reported, as shown in operational block 516.

It is contemplated that a user could use their own mobile device to perform the above function as long as the mobile device has optical sensing capabilities (smart-phone, tablet PC or other mobile device). In this case the mobile device could be arranged and act as part of the exercise machine and would allow the above elements of the invention to be practiced. The mobile device could also be docked directly into a receiving port/docking station of the cardio machine. This would allow the user's personal mobile device to be used to capture data (optically) and then transmit that data to the exercise machine (either through a direct hardwired connection, wireless connection, optical data transmission, or a combination these methods).

Accordingly, the mobile device might have at least one software application that would be configured to detect, then interpret the optical feedback of the user, then process the feedback and convert the data to command signals that would be used as described above. The same software application might also be used to stream content directly to the TV for display from the users mobile device that might reside on the mobile device or that might streamed wirelessly via the users cellular plan or a LAN/WAN offered inside the facility which would allow for 'content on demand' to be displayed directly onto the exercise machines TV display (both embedded TV displays and aftermarket TV displays). The content on demand might include videos, TV shows, advertisements, video games, websites, user specific exercise program information that can be viewed and interacted with, and/or any other digital content the user would like to view and display onto their exercise display unit (emails, pictures, voicemails, etc). It should be appreciated that the exercise program information might be sent via any type of communication method between the user's mobile device and the exercise machine display, where the programming information is displayed to the user and may include the workout information of the user's current session being applied to the program graphical display. This would allow the user to have a better understanding of how they are performing (in real time). This could also allow a user to view (and compete against) other user's program progress on the same or separate display if other user programs were also made accessible for viewing by the user's mobile device for display on the exercise machine display (or any attached display to the machine).

Figure 6:
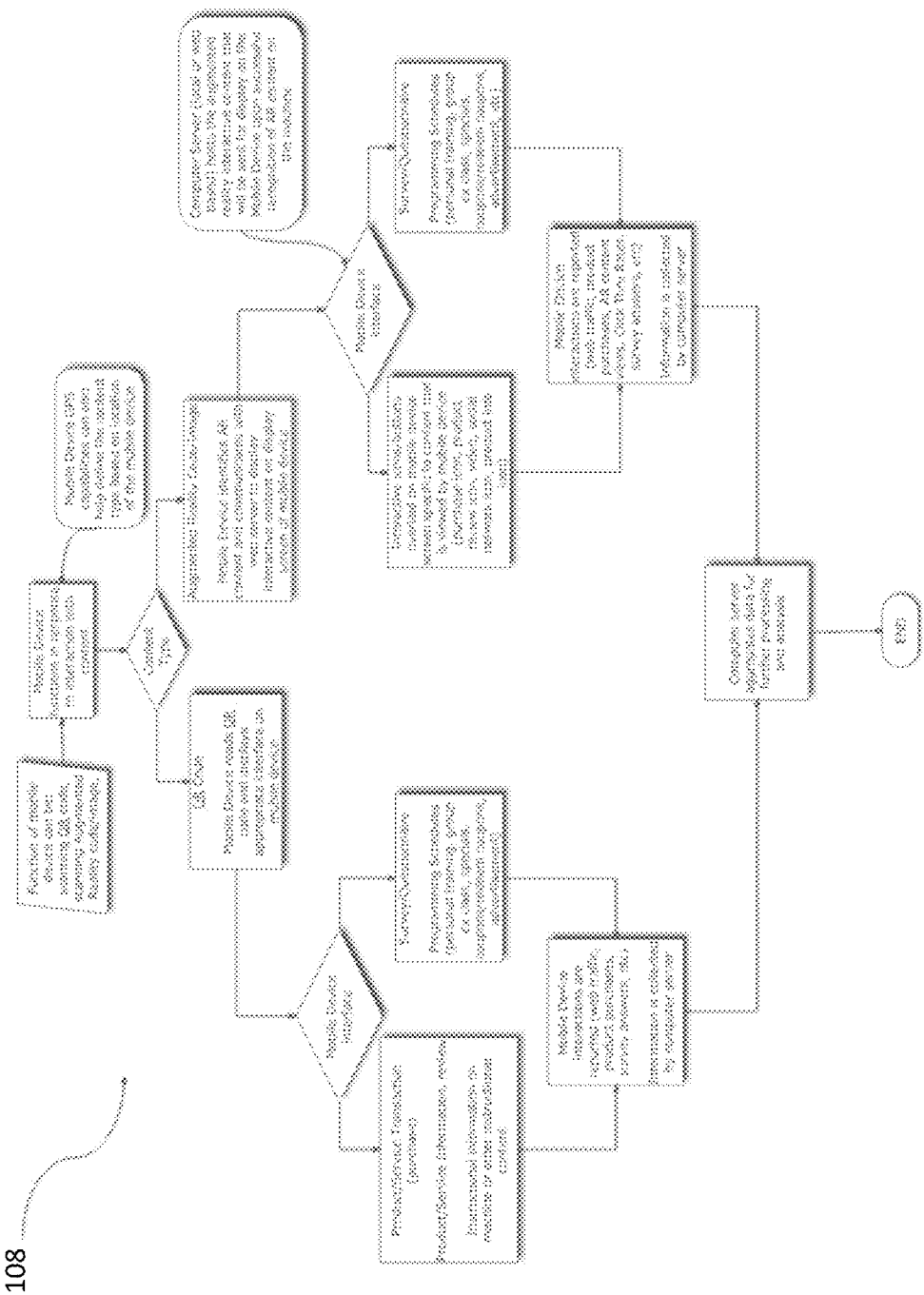
FIG. 6 is an operational block diagram illustrating a general overall method for content interaction with the mobile device, in accordance with one embodiment of the present invention.

Additionally, the user's mobile device might also be able to communicate with both the exercise machine and/or aftermarket TV display unit using anyone of Near Field Communications (NFC) technologies to be able to benefit from what was described above for machine control, TV/GUI control, and content on demand streaming as a part of the optical sensory input of a user. This is advantageous because not all mobile devices (smart-phones for example) will be able to meet the hardware requirements the exercise machine manufacturer or aftermarket TV display manufacturers have for physically docking a mobile device. By allowing the user's mobile device to wirelessly connect to the exercise machine or aftermarket TV display or other peripheral devices using NFC technologies (RFID, Bluetooth, BlueTooth Low Energy, WiFi, ZigBee, Ant+, etc), the system can now allow the user to authenticate themselves on the system based on user profile information that might be stored already on their mobile device. One embodiment of an overall method 600 for content interaction with the mobile device is shown in FIG. 6.

In still yet another embodiment, the optical sensor technology could also capture data from the user such as skin temperature, sweat levels, heart rate by way of skin light refraction/light absorption measurements and methods, etc, where the data can also be used to fine tune machine parameters in real time during the exercise session. This allows the system to obtain data (volitionally or non-volitionally) optically that could control the performance of the workout regimen controlled by the machine.

The data capture approach described above can also apply the data that is obtained to drive advertisements that might be responsive to exercise performance indicators (duration, exertion/intensity, exercise machine performance, evaluation of form during the exercise as compared to a standard for a scoring system). For example, targeted advertisements might be displayed back to the user while they work-out. The advertisements might be displayed by hardware on the exercise machine (LCD display that can receive advertisement data by wired or wireless methods) or hardware associated with the machine, such as aftermarket display screens (that can also received advertisement data by wired or wireless methods such as a display screen. Moreover, in addition to advertisement data, a Gamification backend system might also send data to the exercise machine (either via wired or wirelessly) that is responsive to the performance of the user during the workout session. This would provide a user with feedback, like points earned for their performance, badges, trophies, virtual currencies, coupons that can be redeemed, etc. The user data that can be captured non-volitionally from the optical sensor would be different than the data that might be captured directly from the exercise machine (like from a CSAFE port or USB port) since the data from the optical sensor would have a much higher level of personalization. This is because exercise machines contain standardized software algorithms that make assumptions as to how many calories are burned during a workout (for example). The exercise machine is not able to differentiate between multiple users except by general inputs that might be applied to their software algorithms that are manually entered by the user (age, gender, weight). The optical sensor data would be able to detect skin temperature, sweat level, etc that are the required inputs for true caloric expenditure calculations. Thus, a higher level of motivation would be provided, allowing the user to apply their personalized workout performance data that is optically captured to motivational member rewards and loyalty programs offered to them.

It should be appreciated that an exercise machine that has an aftermarket display that is in signal communication with the exercise machine can benefit from a wireless module that is part of the aftermarket display electronics (the wireless module can be at least partially or fully integrated with the electronics of the exercise machine or the module can be a stand-alone device that by itself is in signal communication with the exercise machine). The aftermarket display may be able to receive data (advertisement data, image data or movie data) from a local computer or one that is connected to the internet or some cloud based data server. The data content can be sent wirelessly for display on the display unit as part of the menu control system display, graphics user interface of the display, or 'picture in picture' capability. This allows for content to be viewed by the user of the equipment without having to place the content on, or as part of, traditional viewing channel programming. This ability allows for a greatly increase capability of messaging and advertising since other systems can only display ad content on a couple dedicated channels, which greatly limits the ability to target the ad placement and viewing of the content by the user since the user can change the channel to watch programming that cannot display targeted advertising or messaging.

Moreover, the data (such as advertising content) might also be displayed when a user reaches a certain milestone (such as one based on their exercise regimen or machine usage). Since the aftermarket display unit is in communication with the exercise machine, the aftermarket display unit (or stand alone wireless module) can have the ability to trigger the timing for when advertising content or other messaging is displayed to the user based on the performance of a persons workout (example: display content when duration values are reached during the session, display content when individual calorie, distance, or heartrate values are reached, or any combination thereof). The wireless module that is communicating with the exercise machine might also be in communication with a local computer in the facility that is running a software application that manages the various content and/or graphic image files. This local computer software program might also have the ability to be connected to third party servers via an internet connection that would allow for content to be dynamically updated, allowing for remote management of content on the system as well as having the ability to report the successful delivery and display of content at the exercise machine or associated displays in a fitness club environment (TV attached to machine, digital signage, etc). The content might consist of graphic images files that are in any digital form to allow for display on the aftermarket display unit or exercise machine display unit (such as, bitmap image, jpeg, PNG, M3, M3, AVI, MOV, SWF, access to web pages displayed, or any rich media file type or static image file type suitable to the desired end purpose).

In still yet another embodiment, the invention may use the facial recognition software to better control the advertising content/messaging that can be displayed to the user during a workout session. In this case, the invention can employ camera technology (webcam, mobile phone camera, etc) that is working with facial recognition software and that allows the system to gather data on the user when they are in front of the aftermarket TV display or on an exercise machine that has either a camera hardware device integrated or externally mounted onto it. The software in this instance may be able to verify the gender and age of the user, allowing this data to be captured and used as part of a calculation that drives what type of image file/advertisement should be displayed to the user.

Moreover, the system may have a software program running on a local computer and/or on the exercise machine (or would be connected to a cloud based system) where the gender/user specific content would be streamed for viewing based on the results of the facial recognition detection process. The facial recognition software might also be able to detect when a person is viewing or not viewing the display screen during the exercise session. This could be achieved by continuously or semi-continuously monitoring the profile image of the person during the working out or by having the facial recognition software be able to detect when the persons eyes are looking at the screen and for how long during the workout session their eyes were fixed on the screen. The reporting outputs of the invention would allow the system to provide data may allow the system to provide enhanced reporting analytics that could be used to better negotiate advertising spend rates with potential content providers since the image files can be controlled for display by using data that reflects what type of person is viewing the display screen and when they actually viewed the display screen throughout a workout session. The enhanced interactivity of the invention also provides reporting capabilities as an output based on how a person interacts with the displayed content using their mobile device (either by scanning a QR code or by using augmented reality software on their mobile device). It should be appreciated that the functionality of the camera can be used with any type of mobile device (smart-phone, gaming device, etc) that might be in electronic communication with the electronic display hardware (aftermarket TV unit, embedded exercise machine display screen, etc). It should be appreciated that the functionality of the camera can be used with any type of mobile device (smart phone, gaming device, etc) that can be in electronic communication with the electronic display hardware (aftermarket TV unit, embedded exercise machine display screen, etc).

It should be appreciated that the content that is displayed to a person while on a machine can give the person the ability to interact with the content using their mobile device by either scanning the content that might have advertisements with QR codes that would link their mobile device to websites (or through mobile device software application interface) to allow further interaction with content (example: purchasing, scheduling training appointments, product reviews, etc). The person might also use an augmented reality software on their mobile device that may further enhance their ability to interact with the displayed content (example: LAYAR), where the mobile device would be able to detect the images from the content which would then cause the mobile device to display an interactive user interface on the person's mobile device specific to the recognized content. This would allow the user to have options such as purchasing product, reading product reviews, sharing content with their peers, sending information to social networks, scheduling training appointments, earning points for rewards programs, etc.

It should be appreciated that when the workout regimen is completed, the user can then scan the dynamically generated barcode. The contents of the barcode that is being displayed might include a single data type set (only advertising info or only workout data) or it might include a combination of workout data history, machine performance information, and/or information on the various advertisements/content that the user viewed during their workout session (coupon codes for merchandise/services, a reference code linking the advertisements to the actual images that were displayed, etc). By capturing this information, the system provides a unique method for generating feedback to an advertisement content provider system that can show demographic information relative to the people that are actually viewing their advertisements. Moreover, the system may also incorporate Gamification techniques to motivate the user to scan the barcode or AR image. For example, a user might generate points (like a frequent flyer program) for every barcode they scan. When the user reaches certain thresholds, they might have the option to redeem the points for rewards/prizes through a rewards program. The user might decide not to redeem the points until they reach the next level (i.e. 'bank' the points), which might be worth more as it can provide a more valuable prize as compared to the last level they reached. The user might also decide to 'gift' their points to another person (inside or outside the fitness centers customer base). This interaction could also be used to promote new membership joining which can be used for member retention purposes.

The invention also contemplates being able to use a stand-alone device that is in signal communication with the exercise machine either through a hardwired or wireless connection (or both) where the stand-alone device (being referred to also as a information processing and generation module) can retrieve the exercise and machine performance information (such as through serial communication with the exercise machine). The information processing and generation module can request the information from the exercise machine and append (or integrate) the incoming data, process the data (packetize), and also might encrypt data (as an option for further data protection), and then generate a barcode (or any digitally generated image that has been described earlier by the invention, on include but not limited to AR codes or HCCP codes). The information processing and generation module can also passively receive the information from the exercise machine, where the exercise machine may send the information to the information processing and generation module (via hardwired or wirelessly connection) without any request from the information processing and generation module. But the information processing and generation module would have the ability to receive and store the information, to append and process the data, and possibly encrypt the data (if desired), and generate a barcode.

The information processing module may also have the ability to create the format of the barcode image where the barcode might have at least one embedded URL inside the barcode which could be used as described earlier for facilitating the flow of data transfer when the barcode is scanned by the mobile device or used as an authentication method for a mobile phone application, where the URL may be linked to the mobile phone application and may allow for data to be captured once the URL is verified. This is advantageous since the URL can be unique to a fitness center location or entity for where data embedded inside the barcode could be sent to upon scanning the barcode. Moreover, the information module might also have a communication port (serial port, USB port, or Wireless connectivity ability—wifi, Ant+, BlueTooth, Zigbee, NFC-RFID or other) that would allow the module to receive updates from peripheral devices such as USB flash drives, mobile devices (such as smart-phones, tablet PC's, iPad) or a computer, where the mobile device and or computer would be able to change the URL information (or other information such as club ID code for example) to allow for a customized solution.

The information processing and generation module might also benefit from having a firmware update or firmware command change from this second communication port/ability where the module can receive a signal (either through a hardwired connection or wireless connection from at least one of the above peripheral devices), where the signal could instruct the information processing and generation module to change operation from its default firmware operation to accommodate a change in firmware operation that would further enable its ability to periodically retrieve or receive information from the exercise machine. This would allow the information processing and generation module to adapt its communication abilities (on the fly or on demand) with the exercise machine (or peripheral devices that are attached to exercise machines that contain sensors that collect, store and process data like on strength equipment or spin bikes).

Additionally, the information processing and generation module may be in communication with at least one of the peripheral devices where based on the results of any possible communication failures due to the availability of information from the exercise machine, the module could request a firmware operation update from the peripheral device (in one example, wirelessly request this info from a local computer running software that would dictate the appropriate firmware operation change), where upon receiving and processing the request from the module and based on the results of the communication failure the module sends to the peripheral device, the peripheral device (ex: local computer) could send a signal to the information processing and generation module that would modify the operation of the firmware on the module that would then allow for successful communication with the exercise machine. Furthermore, the above information processing and generation module can have the ability to send the generated barcode image for display on an aftermarket device on an exercise machine. In this instance, the module would be in signal communication with the exercise machine (for example, using the CSAFE communication port or a USB port on a exercise machine), where the module would generate the barcode image based on the results of the incoming data from the exercise machine as well as from any other inputs (such as graphic image content images or media files that are communicated from a peripheral device to the module), and the exercise machine would have the appropriate software and hardware abilities to simply display the output image file of the module by receiving the image file(s) back through the same (or secondary) CSAFE port or USB port on the exercise machine.

In addition to the module being able to send graphic image files (ex: bitmap image of a barcode or ad content or messaging), the module can also send the information to the exercise machine (or any aftermarket display unit) in the form of a composite video signal or other video output type (RGB, S-Video, Component video, HDMI, etc). It should be appreciated that the module may be in communication with the exercise machine via a hardwired or a wireless connection. Thus in accordance with an embodiment of the invention, a hardware (or software) module that plugs into (or communicates with) a communication port on an exercise machine is provided where the module retrieves data, generates a barcode image file, and then sends this image file back to the exercise machine (or other device) for display of the barcode image. This advantageously provides a solution to simplify software integration. The module would also be able to pass along messaging/advertising content that is sent wirelessly for display on the exercise machine or other device, as well.

In accordance with the present invention, the barcode data may include any type of information suitable to the desired end purpose. For example, the barcode data may include data entered by hand into the mobile device, machine type and characteristics, date/time stamp for the workout/data transaction (this might entered into the mobile device as well if the machine is not capable of creating this), TV channel viewing information (channel viewed, duration of viewing, facility location ID (club ID code), MAC Address info from WIFI hardware that identifies the specific machine, embedded points/rewards output based on workout performance (Gamification output), user ID info (from manual entry or from some external device that uses wireless/wired technology to input a user ID number like RFID key fobs and USB device serial number, manufacturer type, calories, duration, speed, heart rate, incline, exercise program info, resistance, distance (vertical and horizontal), all info related to the health and performance of the machine (such as error codes, utilization, serial number, software version info, etc), advertising or messaging info that is displayed and streamed by the machine interface that might be sent from some $3^{rd}$ party advertising/content management source (local PC or networked server) that is directly wired into the machine or sent wirelessly). This would advantageously allow a fitness center to display messages to a user that can be scanned onto their mobile device (such as coupons, programming information, promotions, events, etc).

Additionally, this would allow the system to provide a tracking reporting solution for member messaging since the user could interact with a message via their mobile device, where the interaction on the mobile device can be tracking by scanning barcodes or content that is linked to an augmented reality server. It should be appreciated that a user's mobile device can also have the ability to tag a data packet that is being sent with specific user information, where the user information may include (but not be limited to) credit card number, license number, phone number, phone serial number, unique ID, code specific to the user, bio-metric digital fingerprint specific to the user, GPS co-ordinates of the user from where and when the scan took place of the barcode, etc. . . .

The messaging content data set could be anything and might be a member questionnaire about how they like the facility, equipment, staff, etc. This can be useful for helping retain memberships and provide motivation for the user to participate in such content programming by adding a reward system into the mix. Additionally, the data set might also contain 'data hooks' that can be linked to various gamification platforms to allow for a more seamless integration of health related data into the gaming platform, since the data output that is directly output from the machine might also support 'virtual currency' calls for a gamification platform that is typically used to handle all currency related transactions and processing for mobile and web based applications. This would benefit developers since it would provide a standard approach in how to incorporate Gamification principles/standards into health related data output systems, and could be used to create a standardized approach that could be adopted by other systems that recorded health data and had motivational/game based incentives as a component.

For example, 'gamification' can be seen in this invention as using inputs (workout performance data) to create a new type of output directly at the machine level, where the machine is now capable of processing the workout performance data and based on the result of that processing, creates a multitude of outputs that provide an easier method for a user to better understand their performance. To further explain, a typical workout that might have an output of 300 calories, 22 minutes, and 3.2 miles on an exercise machine might now be displayed as 75 Points, or a symbol such as a virtual badge or trophy, meaning the multiple data outputs of a workout are now being represented as a single value that has a greater meaning to the user (like a FICO score). This new output can now become part of the barcode data string and can be used by mobile and web based applications to drive reward systems. As is known, reward systems typically require an input, where the input may have a pre-defined value to the rewards system. In this case, the pre-defined value might be the actual 'points value' that is part of the barcode data string. This 'points' input can be used to drive a 'virtual currency' system as part of the invention, where the points output from the machine can be used by a person to purchase items/services, etc.

It should also be appreciated that, as discussed above, the method of the invention allows a user to scan (or take a picture of) the barcode from the machine at anytime the barcode is available for scanning. This advantageously allows a user to append data to data already existing on the mobile device (such as data from multiple exercises in a single (or multiple workout sessions). Moreover, the invention allows data to be appended or combined with existing data as desired, such as via an algorithm, day/date/time, sequence, exercise type, machine type, etc. For example, the machine would be able to identify a data characteristic (such as a sequence number or an exercise type) that would tell the mobile device how to append or combine the new information with the existing information upon scanning the barcode. Additionally, the data code packet that is formed into a barcode can also have a unique session number generated that will help create a unique session. This would be useful in creating a system that could limit the number of times a barcode may be accepted by the system since upon a successful scan and data send transaction, a second attempt to scan the same barcode would fail because the system has already seen the exact contents of the barcode data string.

Additionally, in still yet another embodiment the size of the barcode would be automatically scaled and displayed on the machines digital display to allow for maximum data storage. This is because the size of the barcode might change based on the amount of information that is being used to create the barcode. Thus, limiting or scaling the size of the barcode to the machine or mobile device provides for better utilization of the barcode technology thus allowing users to capture more data directly onto their mobile device. Accordingly, the size of the barcode would be automatically scaled and displayed on the digital display of the machine to allow for maximum data storage. Additionally, tones or other sounds may be used to communication information. (we might have enough on this already)

In still yet another embodiment, the method includes being able to scan augmented reality (AR) codes and content (images that are linked to a augmented reality server) that can display (or cause the device to display) various images, text, video, etc onto the user's mobile device. For example, rather than carrying a service manual for each exercise machine that is being serviced, a service technician that works on exercise equipment can scan an AR code displayed (or a code that is printed on a label) on the exercise machine being worked on and have a 3D image of that machine be displayed on his mobile device. Common accelerometer technology that is inherent in mobile devices would allow the service technician the ability to manipulate his view of the 3D virtual image by moving his mobile device in various directions. By doing this, the service tech would be able to see a configuration of components of the machine that he might not otherwise have access without taking the machine apart.

Additionally, if the machine has self-diagnostic capability, the image that the machine displays might be specific to a certain failure mode, allowing the mobile device interface to highlight which part is malfunctioning to assist the service technician in locating and repairing the problem. Thus, the service technician could select components on the virtual display of the mobile device that might require repair, allowing him the ability to also understand what tools and equipment are required to perform maintenance. Furthermore, the service technician can select components (by touching the component on the virtual display) to get information on specific components which would be displayed to the technician. For example, specific information on a component might include when that component was made, the service history on the system/component, when the component should be replaced based on usage, wear and tear, or perhaps the error codes that the machine has been reporting can create a visual color coded indicator that the component is in danger of failing (i.e. the component may turn red or another color). This method also provide the ability to link the mobile device to online systems that can provide information and video tutorials related to processes on how to repair the equipment as well as purchase replacement parts.

Having the service/operational history for the machine and its components directly available from the user interface on his mobile device would allow the service technician to maximize the time and efficiency to resolve and repair issues. It should be further appreciated that this method can also be applied in many other industries, such as aircraft/aircraft engine repair, medical diagnostic equipment repair, vending machine repair, automobile repair, electronic device/computer repair, manufacturing equipment repair, or any industry that can benefit from the above method.

Another embodiment includes the ability for a mobile device application that allows the user to scan a digital display of a machine using their mobile device. Using Optical Character Recognition (OCR) technology, the application would be able recognize the language that is being displayed on the machine and automatically translate the language that is being displayed (such as English) into a desired language (such as French) that the user would like to or is able to read. It should be appreciated that the method of the invention can also be applied to other applications where the need for multiple language support is needed when interfacing with equipment that displays information on a digital display. This could come in handy particularly for service technicians of different origin as well where equipment manuals that are not in the native language of the user.

It should be appreciated that the method of the invention can also be applied to mobile health devices that have an ability to obtain/generate/capture data (such as bio-metric data). One example includes travel to foreign countries where translation of medical data may be needed or beneficial. In one situation, a person might use a glucometer for monitoring their blood sugar levels, where the glucometer may be able to generate and display a barcode that is generated in response to the user's blood glucose measurement. As discussed herein the generated barcode can be uploaded (i.e. scanned or email/text (image)) using any mobile device. This is beneficial because although there are companies that provide BlueTooth enabled glucometer products, there is still a large challenge in how these devices can communicate with mobile devices due to several reasons, such as mobile device $3^{rd}$ party software development restrictions and limits of data sharing on those devices with $3^{rd}$ party hardware devices. The present invention allows a person to easily transfer their data simply by scanning a barcode that is generated in response to their measurements to a mobile device or other processing device.

The data that could be displayed inside the barcode specific to a measurement taken on a device like a glucometer could include the following: manufacturer ID, model type, sample detection technology code, calibration info of the unit during the sample reading, number of readings taken across a pre-determined time period, test strip type used with sample (enzyme configuration, etc), multiple sample readings all having the above data sets, the actual sample reading value specific to the test type of the health monitoring device, environmental information specific to when the test was performed (temperature, humidity, altitude, or any other significant environment reading), URL for where the data should be sent. The data string inside the barcode might also be generated by a person using a button, touchscreen, voice control interface as part of the glucometer or any device connected to the glucometer. This would allow the person to selectively display a barcode specific to their input. For example, a person might be able to speak into the glucometer that had the ability to convert speech to software code, where the speech input would be part of the data string creation process for the barcode (example: 'display last 17 days readings', 'display test strip purchase barcode', 'display test results trending barcode', 'display augmented reality image').

It should be appreciated that the amount of data that can be sent along in a single scan could also employ the use of 'character referencing', where single digits (alpha/numeric) could be generated and displayed in the barcode where the single character might represent a value of greater than one digit. Barcodes can only hold a finite amount of data (alpha/numeric). To maximize the amount of data inside a barcode, we can have a data set output be linked to a single character. For example, a heart rate value might contain three digits (150 bpm), where a single digit character ('A') could be referenced to equal the value of 150 bpm. When the barcode is scanned, the mobile device or even a web application would convert the letter 'A' back to 150 bpm. The character string for '150 bpm' has 6 characters in it, where as now we would only need one character (i.e. the character "A"). This provides the ability to pack a lot more information into a barcode that might be displayed on smaller devices, such as pedometers, glucometers, etc. Thus, this allows for improved abilities of holding more data inside of a dynamically generated barcode, where the reference characters would be scanned by the mobile device inside the barcode and would be converted to their full digit equivalent either on the mobile device after scanning using a software application or on a backend server capable of the same conversion.

Moreover, Augmented Reality barcodes or images on or displayed as part of the glucometer (or any mobile health monitoring device) can also be used to display interactive images on the mobile device of the user. Thus, when a user scans their glucometer reading barcode, an AR powered image can appear on their mobile device that might let them order more test strips, or other required testing supplies such as lancets, for future readings or could also be used to inform them about new services or products relative to their health condition, specific to the user performing and capturing the results of their glucometer test by scanning a barcode or AR image using their mobile device. Additionally, the invention can be used to create a motivation system/program for the user where the user may be rewarded and incentivized for scanning their glucometer readings onto their mobile device, where each time they scan their reading, the user might earn virtual points that can power a coupon redemption system (such as from third party sponsors like (retail stores, Nike, Adidas, health insurance providers, etc). Furthermore, the invention can be used to provide monetary incentive programs based on the participation levels of the user as it relates to the user using the measurement device and then also capturing their data or results off the measurement device using a method such as the barcode scan method (or any method such as wireless or direct data sync via hardwire connection) to a mobile device or computer.

In addition to a glucometer being able to display a barcode that represents blood glucose or other data points, it is contemplated that the invention might also be embodied as an aftermarket electronic device that can be in communication with the glucometer, either through a hardwired connection and/or a wireless connection. One example includes the already described approach as to how aftermarket devices can retrieve data, process data, and then display data relative to capturing data from devices such as exercise equipment. In this case, an aftermarket device can be in signal communication with a device like a glucometer (or any other biomonitoring device such as a blood pressure cuff, pulse oximeter, heart rate belt, watch device that captures biometric data, pedometer, etc) where the aftermarket module has the ability to explicitly request or passively receive (or a combination of both) data from the glucometer. The module can retrieve the glucometer data at any time, and process the retrieved data as a dynamically generated barcode as it has been previously described earlier in this invention, and then display the barcode on a display. This barcode can be displayed as part of an electronic display on the aftermarket module or as part of a secondary module that is in signal communication with the aftermarket module and that has the ability to receive the data and display the barcode.

It should be appreciated that the aftermarket module might fit the profile of the meter (like a mobile phone case for example), where the module is acting as a case for the glucometer and can be directly plugged into an existing serial port that is part of the glucometers embedded electronics. The module may contain at least one appropriate software communication protocol that would allow the module to communicate with the corresponding glucometer (ie medical monitoring device, fitness tracking device, machine diagnostics device, etc). Moreover, the aftermarket module might also have near field communication abilities that can wireless communicate with a glucometer that also has the corresponding near-field communication abilities (NFC can be any wireless technology: RFID, Bluetooth, Bluetooth low energy, ANT+, Zigbee, WiFi, infra red, microwave, cellular, etc). This would advantageously allow the aftermarket module not to have to be plugged into any glucometer communication port, but would still allow the module to retrieve the data and process for display as a barcode.

It should be appreciated that, in the event the mobile health device (such as a glucometer) does not have the ability to generate/display a barcode in the traditional 'white/black' format due to an LCD screen display, the method of the present invention includes the ability to have use traditional 2D barcodes. For example, the mobile health device might also be used for scanning traditional barcodes. Additionally, the method of the invention includes being able to upload (such as via scanning, OCR, etc.) non-traditional barcode data and processing the non-traditional barcode data to convert that non-traditional barcode data into a traditional barcode standard format (and vice versa). This "secondary processing" might take place on the mobile device or on a remote server running an application that is capable of such processing. Additionally, a person using a mobile device with picture/scanning/OCR abilities might also be able to take a digital picture of the display screen of the mobile health device and process the image using less complicated data recognition technologies (like OCR). This processing might take place on the mobile device or on another processing device capable of such processing.

It should be further appreciated that the method of the present invention may be integrated, in whole or in part, with an exercise machine (or other machine from which data is being gathered) and/or it may be practice via an add-on component (such as an after-market solution) to an existing machine. For example, as a user performs their work-out regime on a cardio machine that has the ability to generate and display a barcode (either internally on a screen display or externally on an after-market screen display), the barcode data string is constantly being regenerated as the workout data is being updated. Thus, a user may begin with '0' calories burned at the beginning of their workout and burn 10 calories/min during their work-out which may last 20 minutes. In this case, the barcode data string may be re-generated every time the calorie burns values are update and available or the barcode data string may be re-generated and then the barcode is displayed at the end of the work-out or the barcode may be updated during the work-out at predetermined (and changeable) periods.

Accordingly, this present invention allows for the capturing of data (biological, machine, performance, environmental, user viewing experience, etc.) related to a specific type of machine (for example, strength, cardio, pedometer, glucometer, etc.), work-out (sets, reps, distance, weight, etc.) and/or biology of an individual (fat content, heart rate, pulse, oxygen level, etc.) and the generation (and updating) of a barcode that is responsive to the data (in whole or in part) captured. Additionally, the data may include data related to the overall performance of the machine (asset info), such as error codes, mileage, total utilization, number of times machine has been used, etc. In accordance with the present invention, this ability to capture and display machine asset data is beneficial to the maintenance personnel who can use a mobile device to quickly and accurately capture important machine asset data automatically without having to manually write down information. This machine asset data may then be processed via a mobile device or it may be uploaded to a remote server for processing (such as for diagnostics) and/or as desired for documentation and record keeping. In addition, the barcode that is generated specific to the machine asset data may also contain instructions and may also have at least one URL (via a hyperlink) to cause the mobile device to display/play specific maintenance videos for that given machine. For example, when a service technician uses the mobile device to scan the barcode on a machine that is being serviced, the instructions contained in the barcode will cause the mobile device to access, display and play a video on how to change service the machine (or change a component, etc.). This video might show information such as the types of tools the person will need to fix the machine.

One way this may be accomplished would be by scanning a QR response code (QR Code), which is typically used in marketing materials for linking magazines/newspapers/tradeshow booths to content via a Universal Resource Locator (URL). In accordance with the present invention, the QR code/2D code may include a URL embedded within along with instructions for the mobile device to auto-direct data transfer between the mobile device and a remote site. Thus, the QR code might also direct the user to a URL which has an entire list of videos related to the machine to choose from. For example, the videos may include instructions on how to perform maintenance on a specific machine. Additionally, the method of the present invention is also beneficial in other areas as well. For example, the staff of a fitness center may use the method to monitor the maintenance history of their exercise equipment, since the barcode scanning can be used as a tracking system for how often their maintenance team works on the equipment. This ability to capture machine data can also be applied to other types of equipment such as industrial machinery, vending machines, medical diagnostic equipment (i.e. CAT SCAN equipment, MRI equipment, etc). Another benefit is that a service technician can selectively network the machine type when the barcode is scanned, allowing for diagnostic updates into the remote monitoring system when service is performed, where the service technician's mobile device is also in electronic communication with the machine.

In still yet another embodiment of the invention, a mobile device can use the method of the invention as a way to send data that might be generated from equipment, such as medical diagnostic equipment (glucometer, DNA Sequencers, hematology equipment, urinalysis equipment, pathology equipment, etc). One benefit of this application involves the fact that these types of devices might not be networked due to security issues and laws. If the diagnostic equipment is able to generate a barcode that contained the results of their tests, a patient can scan the machine only readable code with their own mobile device. This would allow the patient to send their test data to multiple sources and destinations as they desire for parallel diagnostics (their DNA, personal doctor, personal data file, electronic medical record, health insurance provider, etc).

Still yet another embodiment includes a mobile device that has the ability (whether through embedded electronics or by secondary plug in devices) to capture the biometric data of a person (such as fingerprint, heart rate, DNA, etc) and use this method as a way to identify the user and link this identification information to data contained within the mobile device or uploaded to the mobile device. This would provide a real time method of authenticating a person as to provide proof of data ownership and could be used to help secure data as part of electronic records. The data from the above can also be appended to and/or integrated with the data inside of the barcode for user ID purposes.

Still yet another embodiment involves using the barcode that is scanned from a machine (such as an exercise machine) to cause the mobile device to provide information (such as instructional information) to the person on how to use the machine properly. This information might be presented to the user as a video, graphics (images) and/or as text to help the person understand how to operate the exercise machine correctly. For example, a cardio machine might have features of which the user is not aware. The user would then scan the barcode on the machine with their mobile device and the mobile device would display instructions on how to operate the machine. It should be appreciated that this information might be contained within the mobile device (via downloaded application), the cardio machine, on a remote server (via link to URL by the barcode) and/or it might be dynamically generated for the user based on how the user tries to set up the machine. This method can also be applied to any type of exercise equipment (strength equipment, cable based equipment, free weights, suspension based systems like TRX, spin bikes, etc). The barcode can also be used to display information on how to perform specific exercises for that specific piece of exercise equipment or for related exercises that work related muscle groups as the equipment. Thus, this method would allow a person to see a plurality of exercise types related to a specific machine or muscle group. This method would provide an advantage to a person for following a custom designed workout regimen that a personal trainer or expert might have prescribed for them.

Still yet another embodiment of the invention involves the format of the data that is dynamically generated by the system to create a barcode. The method of the present invention can employ the use of data encryption techniques that can be used by the electronics of the exercise machine, so that the integrity of the data of a person is secure as they are scanning the system. This may also be relevant to the business model of how to monetize the health data of a person. By encrypting the data, the invention facilitates the generation of a business model based around licensing of data rights to third parties for having access to the data. One way for a party to have access to the data after scanning would be to have licensed the rights to the encryption key technology from the inventor (licensor). The necessary encryption key can allow third parties the ability to have access to the data where it might be used to apply data to various mobile health related software and machine asset management software applications and may be kept secure as desired.

For example, a gym chain (24 HR Fitness) has thousands of exercise equipment and millions of gym memberships. Revenue streams could be created by the invention by selling hardware to a gym that delivered the barcode generation technology to that environment. Part of that business model would be to license the rights to have access to the encrypted data from the invention, where the data of members could be used to help retain memberships by allowing members to track their workout history or allow personal trainers access to member information to build better client relationships. The gym might also want access to the machine performance information to help better maintain their equipment which would also be a data licensing opportunity.

The barcode (which may or may not be dynamically generated) can contain a URL (or more than one URL) that will allow data (all or only a portion) to be sent or redirected to the specified URL(s). This is advantageous since the user does not have to perform any operation on their mobile device (other than scanning) to have their data sent. Also, this lends itself to the business model of controlling and protecting 3rd party licensing revenue models. Since 3rd parties will have to be granted access to the 'gateway URL' that is specified in the barcode, licensing revenues from 3rd parties may be linked to the data access privileges based on conformance of royalty payments to the provider of the technology. Moreover, Augmented Reality tags/codes can also be used as a part of the barcode display to create 'virtual' interactive images on the mobile device display that might be representative of various URL's the user can choose from to have their data sent to (Nike+, Adidas MiCoach, PHR, etc).

Still yet another embodiment includes linking workout performance of an individual, that is displayed as a dynamically generated barcode, directly to a mobile application advertisement that may be driven off of how a user performed during a workout. For example, if a user workouts for a certain duration, they might, after they scan their workout barcode, see a sponsored app from a third party advertiser that is specifically targeted to the user's profile (gender, age, weight, physical condition, etc). The targeted information might be use to incentivize and provide the user additional motivation for working out by applying their workout data to a rewards system (similar to frequent flyer points). In one scenario, the more a user exercises and captures their data, the more they may be able to grow their real world or virtual currencies that can be redeemed for actual money (physical currency) or coupons from advertisers. Additionally, the advertisers might also be able to take advantage of the mobile devices GPS abilities and display even more specific advertisements based on the geographic location of the user since mobile devices can be used to identify the physical location and address of the device.

Thus, when a user scans a barcode, the data that is generated/transferred specific to that barcode could also be used to generate AR coupons that the user could redeem. For example, a user might exercise for 15 minutes, and based on the duration of their exercise a coupon having a value might be displayed on the interface of their mobile device (or sent to them via email or txt message). If that same user were to exercise for 30 minutes, the user would receive a coupon of higher value that is based on the fact they were physically active for a longer duration. This provides further motivation for a user to exercise for longer durations based on their ability to generate and redeem higher value coupons based on their physical activity performance.

In still yet another embodiment, a barcode can also be affixed to a free weight which would allow a person to quickly scan the dumbbells they are using for exercising. When the user scans the free weight barcode, the mobile device might also apply the captured data to an existing exercise regimen that may be on the person's mobile device, allowing the user to more efficiently track adherence to a prescribed workout regimen. Additionally, the method of the invention also includes processing the scanned data to compare against the user's prescribed regimen, allowing the user to see if the free weight they are using is within the parameters of their regimen. Additionally, if the free weight is not part of the regimen, the user might have the option to accept or decline the input and choose another free weight that is recommended by the mobile device application. This again provides a novel method for exercise regimen instruction. Additionally, the invention may allow for the provision of an audible feedback to the user upon scanning the barcode on the free weight, where the voice/audible feedback might be created and played by the mobile device upon the scanning of the barcode. When the barcode is scanned and decoded, a text software script may be created (or previously created and stored) and converted to speech using a 'text to speech' algorithm. This advantageously allows the mobile device to be able to dynamically generate specific instructions and communicate the instructions to the user based on the inputs of the scanning of barcodes.

It should be appreciated that the barcode data for a free weight assembly might include: Manufacturer, model, weight amount (in kilograms or pounds). Additionally, the free weight rack might also have the barcode affixed to the frame which would also allow the user to scan. This advantageously allows a fitness center to track and ensure that the proper weights are located in their proper racks. The person might also be able to interface with their mobile device to enter in the amount of sets they did for each exercise to further complete their workout log. It should be appreciated that the present invention can also be applied to other types of exercise devices that are not classified as free weight exercise types. For example, a BOSU ball might have a barcode on it that can allow the user to scan, and then view exercise types that can be performed using the device (push-ups, step programs, plyometrics, etc). Moreover, the present invention can be used with exercise apparatus that can be classified as group exercise apparatus's.

For example, TRX training is a type of suspension based exercise platform that allows a person to perform various resistance based exercises using their body weight along with suspension cable systems to create resistance that results in exercise sessions. The amount of exercise types are numerous for this type of system, and a person would typically have a placard that describes general instructions on how to perform the exercise. By scanning a barcode on the exercise equipment that is capable of causing a mobile device to display video or graphical tutorials on how to perform a specific exercise, a complicated training system can be more efficiently explained allowing the person to benefit more from the exercise. The barcode may be affixed to the TRX suspension cable gear or even to a frame that is used to support the suspension cables or, the barcode may be on a placard for the TRX exercise instruction booklet.

It should be appreciated that the use of a 3D barcode might be advantageous since 3D barcodes can be physically embedded or embossed into a plurality of materials (such as the metal supports) versus being printed out on a label.

Still yet another embodiment includes applying the biometric data of an individual to drive 'game based' applications. For example, a user might have a mobile phone application that can convert real world data to virtual currencies or use the real world data to affect the attributes and characteristics of an avatar or environment, where the avatar may assume some or all of the characteristics of the user, machine and/or environment via a barcode that was generated and that was scanned in using the mobile device. One advantage of this embodiment is that it acts to motivate a person to sustain a level of physical activity participation at a higher level than when not applying the biometric data to a game type solution. The real world data collected from this system might also be used to earn virtual achievements set up by the mobile application (or remote server application). These virtual achievements can be used to create a social status inside a community of other players, and even allow the user to share their activity achievements on social networks like Facebook® and/or Twitter®. One advantage is that the user can seamlessly handle data transactions directly from their mobile device (these data transactions may include uploaded workout data, process data for display, apply data to gaming application, send data instantaneously to multiple server side applications).

Another advantage includes the ability to more easily share data across multiple software applications without having to develop complicated backend web services type solutions that are typically used for sharing data between systems. The Gamification application of the data can also be used to create a leveling system for the user, where the scanned data can be applied towards status levels. Thus, in order to reach the next level, the user may have to increase levels of activity or commit to achieving levels of activity participation over a pre-determined time-frame. This creates another layer of motivation for the user and helps encourage a more healthy lifestyle.

Figure 7:
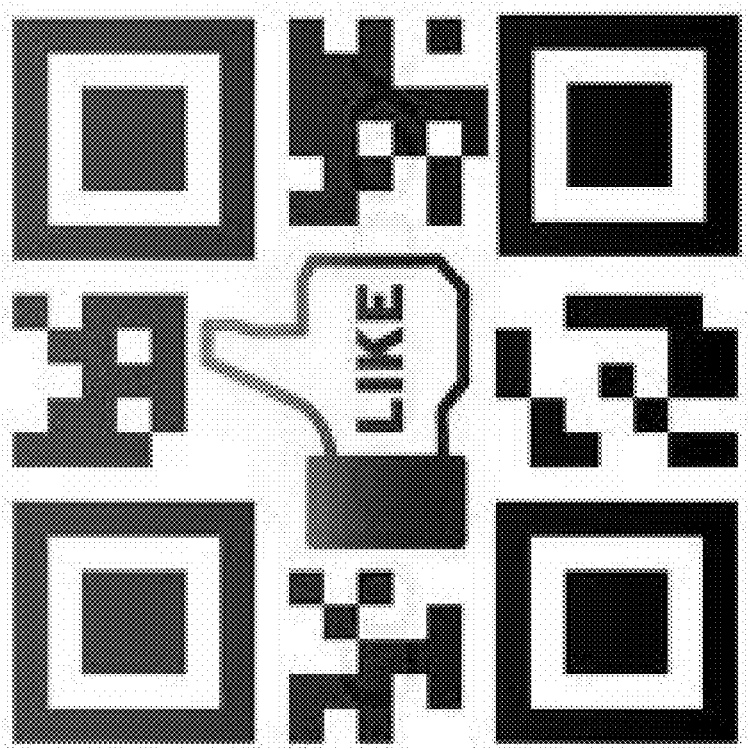
FIG. 7 illustrates a barcode, in accordance with one embodiment of the present invention.

Still yet another embodiment includes having logos, pictures, and/or animations embedded into the dynamically generated barcode (See an example in FIG. 7). These elements might be generated based on the quality of the workout routine that was completed by the user, or they also might indicate the overall health of the exercise machine or be linked to an advertisement or message (overall health of the machine means that the barcode might have a 'human readable' image as part of the barcode. Barcodes are only machine readable and by adding the human readable element as part of the barcode display would help a person understand more about what type of content is inside the barcode) that is displaying the barcode. In one application, this might aid the user in understanding whether they are on target for hitting a specific goal. In another application, if a service technician is working on the machine, the user could quickly be notified (such as via a thumbs up or thumbs down image inside the barcode) that they should scan the barcode to find out more details on the health and operation of the unit.

Still yet another embodiment is related to monitoring the eating habits of a person and involves a person being able to more efficiently capture data relative to their eating habits. For example, most grocery stores have touch screen point of sale computers that consumers will use to check out food from the store. In this example, a person would ring up all of their purchased food, and then have a dynamically generated barcode be displayed on the touch screen display that may include information regarding the food they purchase. This Information may include items such as total fat content, calories, portion sizes, protein, carbohydrates, sodium, etc and can all be captured by the user when they use their mobile device to scan the barcode. This would allow the user to keep track of their weekly/monthly food intake. By allowing a consumer to track this information, the person's food data can be applied to diet programs they are engaged in (Jenny Craig, Weight Watchers, etc), where points are used to dictate the amount of food consumption on a weekly basis. Using the information obtained (such as health condition, diet, nutrition requirements and food nutrition data) the invention may include suggesting foods to eat along with healthy preparation methods and recipes. This would allow the person to better manage their overall food intake by allowing their data to be tracked historically over time and then compared to the diet plan they are on. If the person purchases food high in fat, carbohydrates, sugars, etc. . . . they might receive a notification that their food purchase will bring them over the allotted point (or calories, fats, carbs, etc.) total for a given time period and they should either increase physical activity levels to counter additional food intake or be mindful in their consumption. By participating in a system like this, a person would be able to better manage their diet goals.

In accordance with the present invention, the method may also include keeping track of foods costs along with food content, where the method could suggest menus, recipes and purchase choices to a user based on cost budget, family members, food content and/or time constraints. For example, the method of the invention could be used to help plan meals and thus purchases for a particular time period. Because lower income individuals and families typically purchase food based on their budget, the food is usually not the healthiest choice. The present invention could suggest meals and food purchases based on budget (and other parameters) and thus would advantageously allow lower income individuals and families the ability to maximize their nutrition and health while minimizing their cost.

This method could also be applied to standard paper receipts that are generated in the event a touch screen display is not available during the purchase of their food. By applying Gamification principles, the user might be rewarded for simply scanning the barcode to initiate participation. This would further provide incentives for the person since they might be awarded coupons towards discounts on future purchases or build a social status on a virtual online community that includes other participants. Additionally, if the person visits a restaurant, they can also scan the food receipt that might have a barcode on the paper that represents a report on their specific meal they just consumed. This could also be useful in helping the person manage their diet plan by allowing them access to calorie, fat, sugar, etc intake at restaurants or fast food places. This method can also be useful for people that suffer from chronic diseases such as hypoglycemia or diabetes, where their food intake is critical to the state of their disease and must or should be controlled. By offering a solution that can immediately identify the composition of a food purchase, a person with a chronic disease could be notified by the system via their mobile device (or by any electronic means) that their food purchase is either good or bad for their condition. This information might also be shared with an electronic medical record, doctor, insurance provider, nutrionist, or other expert. Additionally, by sustaining participation in this type of approach, a health insurance provider would be more inclined to review the risk levels based (at least in part) on their ability to report their general food intake history. The more you participate, the greater opportunity you may have for an insurance premium savings. This model fits perfectly into the consumerism approach taken by most health care providers.

Figure 8:
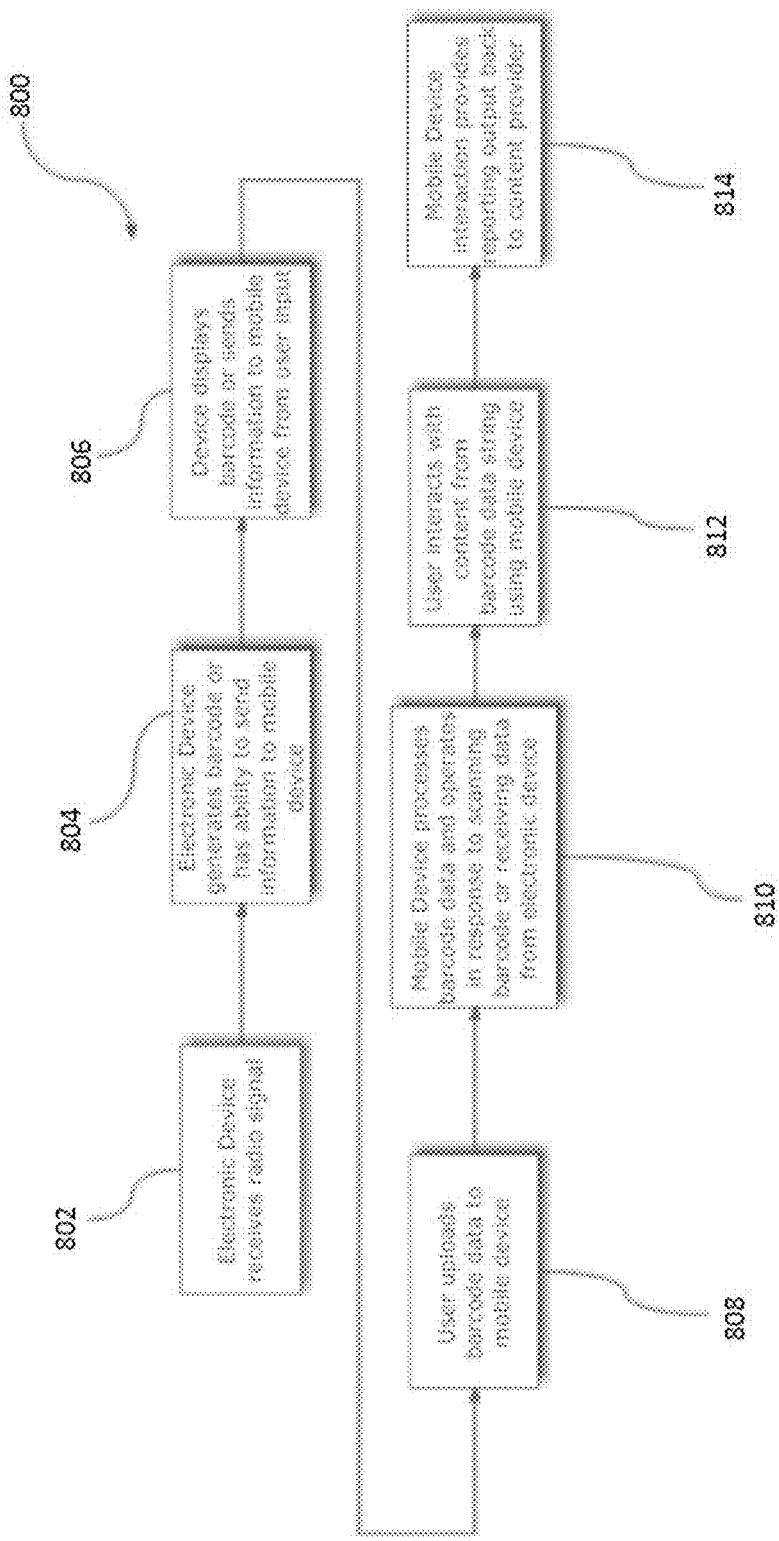
FIG. 8 is an operational block diagram illustrating a general overall method for delivering radio content to a mobile device is shown and includes receiving a wireless signal, in accordance with one embodiment of the present invention.

Referring to FIG. 8, one embodiment of an overall general method 800 for delivering radio content to a mobile device is shown and includes receiving a wireless signal, as shown in operational block 802, and generating barcode data responsive to the wireless signal, as shown in operational block 804. A barcode is generated based on the barcode data and is either displayed or sent to a mobile device for user input, as shown in operational block 806. The user uploads the barcode data to the mobile device, as shown in operational block 808, and the mobile device processes the barcode data and may operate in response, as shown in operational block 810. The user may interact with the content, as shown in operational block 812, and the mobile device may report interaction to content provided, as shown in operational block 814.

In still yet another embodiment, the invention involves using dynamically generated barcodes in regards to secured payment transactions. For example, there are vending machines (such as RedBox®) that allows a person to purchase/rent a movie. Typically, these machines have a credit card reader that the person swipes to make a payment. The same vending machine might also have a digital display that is capable of displaying information relative to their purchase. In accordance with one embodiment of the present invention, instead of using their credit card for payment, the user could use their mobile device to pay for an item by opening a web based software application on their mobile device, where the application has their credit card information already stored. The vending machine is connected to a server and by scanning the barcode being displayed on the interface of the vending machine, this would cause the server to charge the charge the cost of the product to the credit card and release the product to the user. By doing this, the user's credit card information would remain more secure since the vending machine would be able to authenticate the person's payment info via the internet by communicating with a remote server that is also in communication with the user's mobile device software application. Additionally, this method might also provide a good secondary payment solution for the vending machine when the credit card reader might malfunction and not be useable. Also, this method also has the ability for the vending machine vendor and any other parties, to see demographic information on the person since that data might be more readily available than when using a standard credit card.

Figure 9:
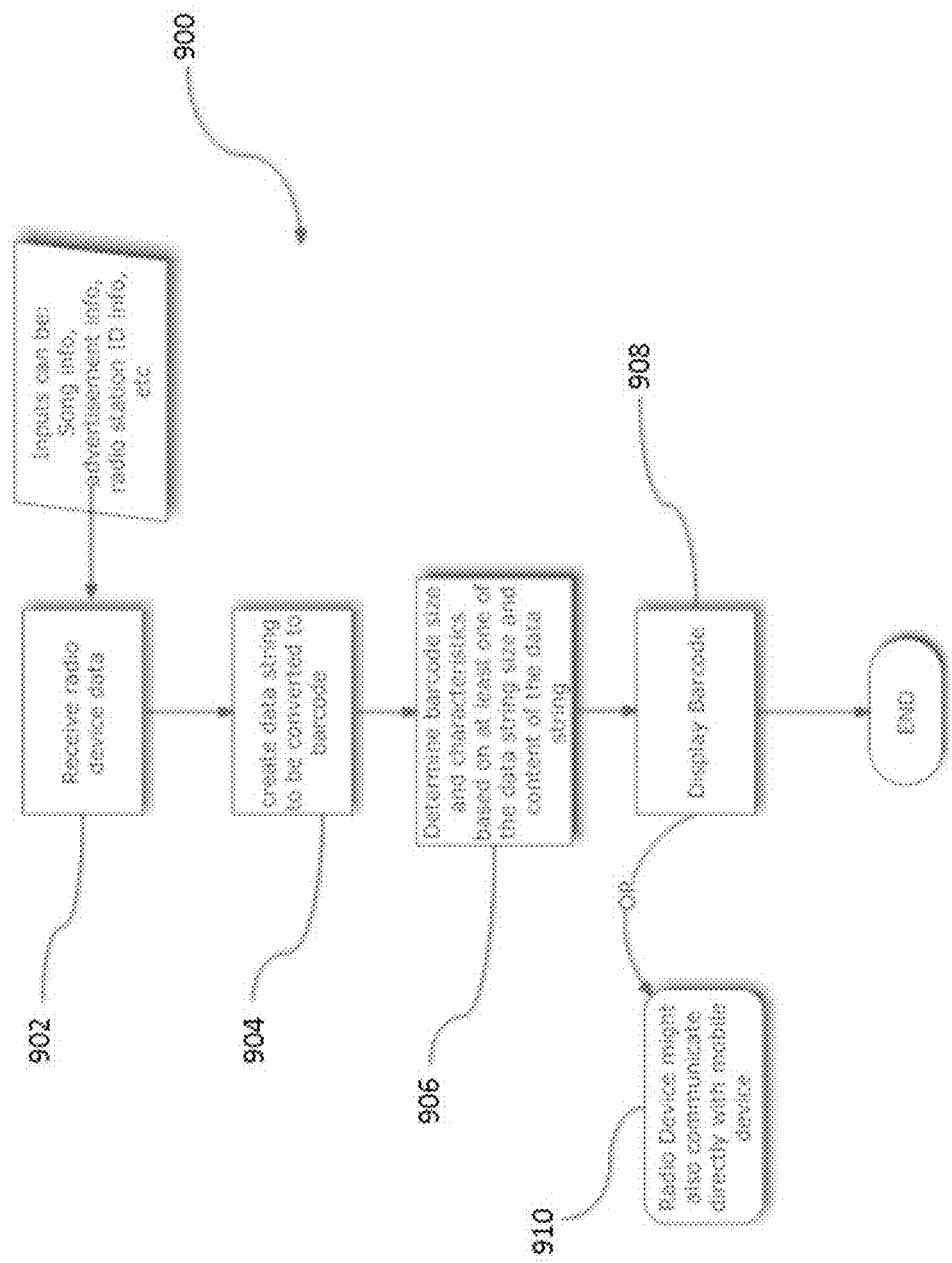
FIG. 9 is an operational block diagram illustrating a general overall method for generating a radio barcode is shown and includes receiving radio device data, in accordance with one embodiment of the present invention.

Referring to FIG. 9, one embodiment of an overall general method 900 for generating a radio barcode is shown and includes receiving radio device data, as shown in operational block 902, and generating barcode data responsive, at least in part, to the radio device data, as shown in operational block 904. The barcode size and characteristics are determined, as shown in operational block 906, and the barcode may be displayed, as shown in operational block 908 and/or the radio device may communicate directly with the mobile device, as shown in operational block 910.

Still yet another embodiment involves data compression content and how the dynamically generated barcode can be displayed in various ways to handle data sets that are not typically capable of being displayed inside a single barcode format. Besides displaying a single barcode that would contain the majority if not all of the exercise performance data of a person, the exercise machine may also display multiple barcodes that may be identified within the barcode as representing various segments of the person's workout. These multiple barcodes could be displayed all at once for sequential scanning by the user or might appear one at time allowing the user to scan each barcode separately. Additionally, the method might periodically flash the barcode on the screen to allow a single scan attempt to capture multiple barcodes all in one scan via the mobile device.

Figure 10:
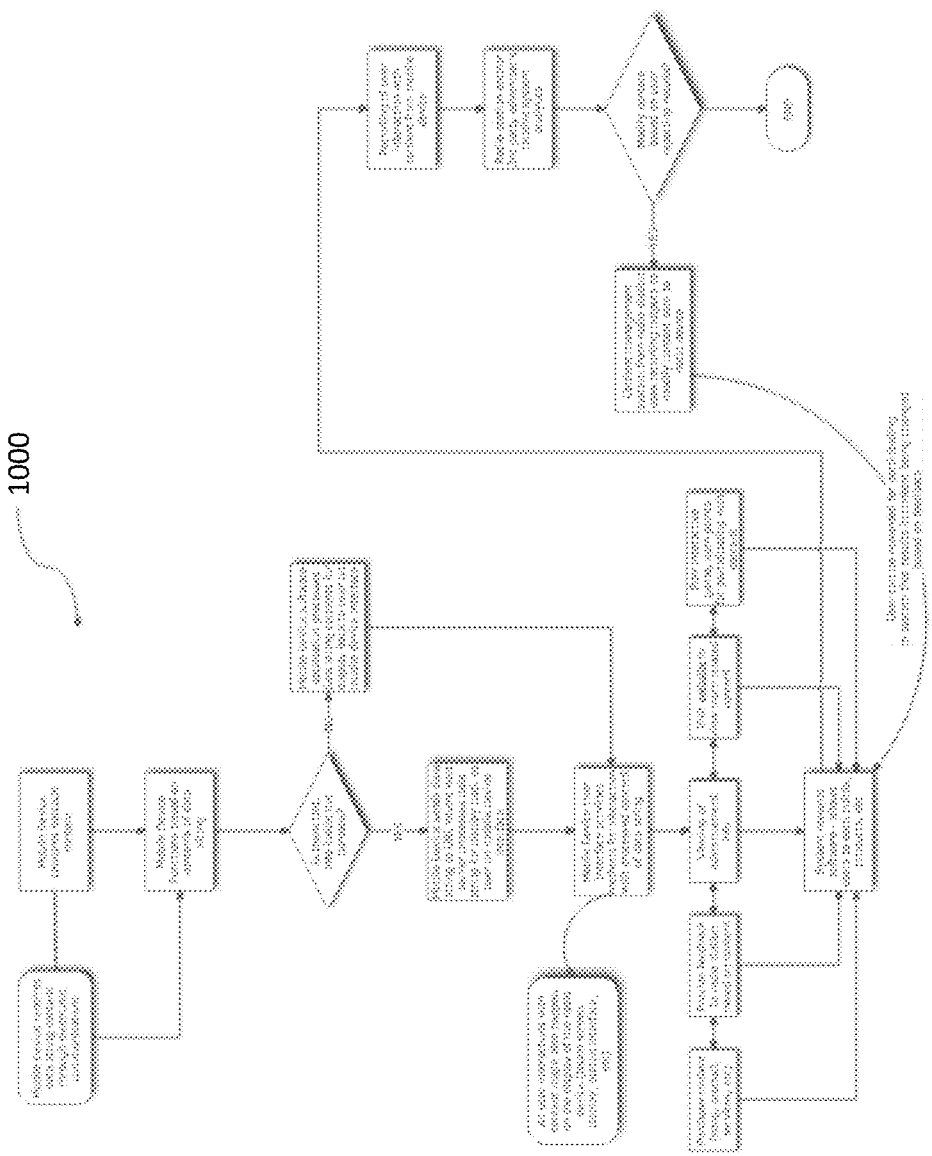
FIG. 10 is an operational block diagram illustrating a general overall method describing the radio-mobile device interaction, in accordance with one embodiment of the present invention.

Still yet another embodiment involves a dynamically generated barcode that could be created by a video gaming system that is connected to a digital display. For example, Nintendo® offers a peripheral device called Wii Fit®. This device allows a person to follow an exercise regimen allowing their performance data to be sensed by the Wii Fit® device, or even by the Wii® controllers that have accelerometers built into them and allows for the bio-metric exercise data to be displayed as a dynamically generated barcode on the users digital display (TV, computer monitor, etc), allowing the user to capture their workout info directly onto their mobile device. This allows for easier access for sharing and storing workout data, so the user might have direct access to their workout history themselves, or they might allow a third party software application the ability to process the bio-metric data from their video game console system and apply it into various software application uses (mobile apps that send data to social networks, create leaderboards, team challenges, etc). Typically, third party developers do not have any access to this type of data and the method allows for the seamless flow of user bio-metric data, where the user is in complete control of the data transfer process. Other exercise video game systems can supply the same solution (Xbox® Kinect®, Playstation® Move, or any other game based product). This method can also be applied to traditional arcade games that are installed in shopping malls and amusement parks. By displaying participation data of an arcrade game using a barcode, the data can now be 'networked' without having to create a physical data connection with the actual gaming hardware. One embodiment of an overall method 1000 describing the radio-mobile device interaction is shown in FIG. 10.

Still yet another embodiment involves video game systems that might be found inside a sports bar, arcade, or other recreational area can have the scores of a play session be generated into a barcode that might be scanned. These machines are typically not networked and only have the ability to display leader boards at a local level for that single machine. The present invention would allow similar machines from multiple locations to have the highest scores networked online by allowing players to scan their scores via barcodes and then submit them for competition. Users could use this type of system to create virtual competitions of arcade based games, allowing for improved level of competition outside of their normal peer groups in their geographical area (or other parameters). These barcodes may also be dynamically generated based on how the players performed during their game sessions (or other parameters as desired, such as age, frequency of play, etc).

Another embodiment involves the format types of the barcode being generated, where the barcode might also use colors as part of the barcode. This will allow for a higher amount of data that can be included in the barcode. High Capacity Color Barcode (HCCP) is one example of how color can be used to increase the amount of data represented by the barcode. Additionally, the use of color can also be used to quickly signify the intensity of the workout by the user (for example: red=too high, yellow=too low, green=just right). Color can also be used to quickly and visually identify the health of the machine as well, allowing a maintenance person to identify whether any error codes are active simply by looking at a color barcode. Color might also be used to identify a facility the equipment is in (by using a mix of color combinations). Color might also be used as part of a 'gamification' solution, where points are awarded to the user for hitting exercise related milestones (number of calories burned, heart rate zone minutes earned, distance completed, duration completed, etc). In this instance, the color barcode may signify an achievement that was earned based on the user's performance. By using a colored barcode approach, the system can more easily provide data to a backend system for displaying information for reporting purposes without the need for intense data processing of encrypted data formats. The barcodes can also be a combination of the standard 'black-white' pixel along with the use of colored pixels to allow for optimization of data formatting by combining both barcode display options.

It should be appreciated that as used herein a mobile device can be a cell phone, smartphone, PDA®, iPod®, iPad®, iTouch®, Tablet® PC or any other mobile device capable of receiving (visually) and transmitting information.

The gaming devices may also be able to generate a dynamic bio-metric barcode which could be displayed on their display screens. These devices have built in accelerometers and other sensors that capture data such as heart rate, as well as peripheral devices that can monitor blood sugar/glucose levels. All of this data can be compiled on the portable gaming device and displayed as a barcode where the user could scan the barcode for processing and/or forwarding.

Still yet another embodiment involves the use of a dynamically generated barcode for the capture of data that may be displayed on a device that is used to listen to radio stations or capture music from a satellite service. When a person is driving in their car, the typical radio display might display the artist name, name of the song, etc that is playing. The present invention contemplates that the radio may display a barcode containing information related to the audio output (ie. artist, author, song, song title, book, interview, etc) where the user would simply have to scan the displayed barcode. The information in the barcode could then allow the user to purchase and upload the audio immediately or the information can be stored for later consideration and purchase. When the person(s) in the car scan the radio display with a mobile device, the software application on their mobile device can store the information specific to the song for review later. Additionally, the same software application can submit an automatic request to one of many internet based music download solutions (iTunes® for example) where a person with a mobile device that can be connected to the music service will have the song selected inside their account for a possible download, at their discretion, at a later time. Or, they can have their iTunes® service set up such that simply by scanning the barcode will prompt their cell phone to start downloading the music they are listening to, directly onto their mobile device. The barcode may be generated by the car radio, by another entity or by both.

Additionally, the use of colors inside the barcode symbol that is generated and displayed by the car radio can help the person driving the car understand how popular the song is by the number of total downloads for that song on a given day/week/month/year, etc. In one embodiment, since users would scan the barcode to initiate the download process onto their mobile device, this can also be used to track downloads by providing data to a backend system from the internet connected mobile device that would scan the barcode since the barcode could also have a unique identifier that might be specific to a radio station, or time of day the barcode was displayed. It should be appreciated that the present invention may benefit from facial recognition technology (OCR) from a wireless sync to a mobile device, benefit from speech/voice input controls by the user into the radio device or mobile device and even a combination of both a wireless and scanning method.

Moreover, the invention contemplates a wireless sync from the car radio device to a person's mobile device, where the user would have a touch screen display as part of their car radio interface. On the touch screen interface, there may be options for a user to press a button on the display to send data information of a song they liked that was currently playing directly to the wirelessly sync'd devices, or the music transaction might start automatically downloading onto the mobile device where it would be stored for future use. Also, this same wirelessly enabled radio display would also have the ability to display the popularity of the song being played to help inform the person that the music is a popular or favorite song amongst other participants/subscribers in the system. The person's mobile device may also have the ability to send specific profile information of the user to the radio display device that might contain preferences on music types, bands, artists, songs, etc. This information could be used by the wirelessly enabled radio device to help filter and pre-select songs for the person based on their preferences. All of the above described tracking benefits for scanning the barcode may also apply to the method of a wireless sync to a mobile device since the user would be able to provide traceability for the content they select by how they interface with the radio device.

Still yet another embodiment may be related to advertising. When a user scans the barcode from their car radio using their mobile device, the user might see a sponsored add displayed on their mobile device that is from a radio station sponsor. The information for the advertisement might be embedded into the data of the dynamically generated barcode or the barcode might contain a URL link for the specific advertisement that would direct the user to the advertisement before they would be able to download the song to their mobile device. This is a novel approach for providing a return on investment (ROI) for $3^{rd}$ party sponsor's that sponsor over the air radio adds by providing a method of tracking the adds that are viewed by using the barcode scan feature. This advantageously allows radio stations the ability to sell air time that is related to music being played since an advertisement can be strategically placed over air time when music is playing. Thus, advertisements can be displayed as the music is playing whereas traditional methods of radio advertising are typically done only in between music sets on a radio station. Accordingly, the present invention allows 1) $3^{rd}$ party advertisers to see a true ROI for their efforts, and 2) radio stations to be able to expand their capacity in their ability to sell advertising time because the advertisements (in the form of a dynamically generated barcode) can be running at the same time as the music is playing. Furthermore, the scanning of the advertisement might prompt an automatic text message to be sent to the user's phone when the barcode from the radio display is scanned. That text message might also be an email or other message variant that is used to communicate the advertising message, all the while allowing tracking of the advertisement back to the $3^{rd}$ party and the radio station for ROI reporting purposes. Additionally, radio stations can create business models around selling music air time that is linked to the most popular songs or even talk show radios.

Moreover, the present invention may allow a user to communicate to the radio station that they 'like' a particular song that is playing. When a user indicates that they 'like' a certain song, the corresponding advertisement data might be displayed directly to the user. The display may have the option to have controls for the duration of the advertisement display before the process of sending the music related data to the mobile device begins. Additionally, the radio device display might also have a list of 'free' content on the device that have been pre-paid for by sponsors. This content might be in the form of music, pictures, videos, games, etc. . . . that might be available for download to a mobile device when the person initiates the transaction of downloading/syncing data to their mobile device. The sponsor of the content may benefit from additional viewing of their advertisements as part of the requirement for completing the download of the sponsored content onto the user's mobile device. Additionally, when the user initiates the wireless data send for the content, the associated data that is sent to the mobile device may also contain $3^{rd}$ party advertising information. This allows content providers (such as radio stations) the ability to strategically place advertising information with the most popular songs for syncing, which would allow the content providers to generate additional advertising revenue by allowing advertisements to be initiated by users of the system as they engage with the system. As described earlier, this system provides tracking and ROI for the 3$^{rd}$ party advertiser since each transaction can be tracked specifically to a user. Furthermore, the reporting metrics back to the content provider and 3$^{rd}$ party advertiser would also provide insight into the demographic information of the user. The advertising information might be displayed on the mobile device as a mobile web page, banner add, sponsor tag, or other method of display. As users engage with the system, they might be rewarded with free uploads if they pay for a subscription to the service. Furthermore, the users that use the service frequently might benefit from free content based on their usage.

Still yet another embodiment involves an interactive user interface of a car radio while listening to content. As a person listens to music, they may have the ability to inform the content provider on the quality of their content (say by pressing a button on the radio display interface that would signify a sign of approval or disapproval). This would allow content providers the ability to apply traditional continuous improvement methodologies to their programming design by using the feedback of subscribers. When the person initiates feedback for the content, the feedback may be sent back to the content provider by wireless communication directly from the radio interface device or by using a wirelessly connected mobile device to facilitate the feedback via a cellular network (or by any other means of data transmission). This feedback could be used to generate popularity ratings for the content that is distributed from the content provider. This feedback mechanism could also be applied more specifically to talk radio where users are typically unable to call into radio stations successfully due to busy lines. By allowing a more open method of communication with the station listeners, listeners can be rewarded for their participation during the talk show session which in turn may reduce the amount of station changing. By applying the principles of 'gamification', listeners might generate social status as part of that talk show by how often they provide feedback on a comment or topic that is being discussed via the interface on their radio device.

Additionally, the user's mobile device may be used to provide a user ID data set for each feedback response back to the station, which would allow the content provider the ability to track who is actually providing the feedback. This method of tracking the feedback data can be used to create a user leveling system that is designed to engage the listener to promote loyalty and 'stickyness' for the content provider. In addition to a leveling system, specific achievement levels could also be created that are based on the amount of content that is sync'd from the radio device to the mobile device, or by monitoring the amount of time the person is listening to the radio station. This game-based mechanism may promote adoption of content transfer by the user as part of the system since it will further create a unique social status that could be shared with other participants of the system via a website or social media platform (Facebook/Twitter for example). The system may also reward users for when they would bring in or refer their friends or others into the service through sharing their experience by either interfacing with the radio interface or by using their mobile device to share their performance on the system with their friends and contact list.

Additionally, the radio station may be able to offer specific meta-games that would promote user listening since the users would be incentivized to 'play' the game by staying tuned to the station for a duration of time. One example of this might be where a radio station solicits an advertiser (example: Budweiser®), and when the name of the specific sponsor is mentioned by the radio broadcaster, the user would enter feedback into the system either by their radio device interface or by their mobile device. The radio broadcaster would then be able to tally up and report back on how many users participated and achieved the maximum number of feedback points based on the number of times the sponsors named was mentioned during the 'game'. The result of this game based listener participation strategy would be a further detailed understanding on the demographics of the users who are listening which may leads to a better ROI for the advertiser.

It should also be appreciated that user/listener feedback, while it has been so far described as being submitted by interfacing with the radio display interface or the user's mobile device, can also be submitted into the system by voice, sound, and speech activation. The radio device, the user's mobile device (or any mobile device in proximity to the radio device or by itself), and/or other peripheral sensory interfaces (steering wheel embedded controls, blue tooth headsets, GPS units, etc may be used to support the feedback interface as well as the voice activated feedback solution. Moreover, this approach could be applied to rank content that is traditionally ranked by the content providers (example: American Top 40 Pop music list). By allowing the content feedback system to control the ranking, new and upcoming artists that might not have traditional methods of obtaining status due to traditional ranking metrics might find themselves on a 'Top 40' list, granting the artists accelerated recognition for their content. The radio content providers backend system would be able to process the feedback accordingly and then display updated rankings on a predetermined time basis that corresponds to their programming schedule.

Still yet another embodiment involves the ability for a mobile device to share content from the mobile device directly to the radio device. This would allow for user generated content to be potentially distributed to the radio content providers (radio stations). This might be in the form of a video taken from a mobile phone, voice note/recording, picture, media content such as a MP3 file, music, streaming video, etc. The content provider would then be able to (at their discretion) redistribute content from the user base to the entire user population. This content may be available for viewing or download by other users either on the radio device or on another user's wirelessly synced mobile device. It should be appreciated that although the use of wireless data transmission and barcode scanning has been described, other methods of data transmission can be used to achieve the same desired result (physical data connection between radio device and mobile device, USB (means mobile device is plugged into radio device), Zigbee, BlueTooth and all variations of BlueTooth, Wi-Fi, RFID, Infrared/Microwave, etc).

It should be appreciated that in still yet another embodiment, the barcodes might also include links to a social media site (like Facebook® or Twitter®), or other website which by the simple act of scanning the barcode from the radio display may create an action that may link the person scanning the barcode to the end destination website. For example, scanning the barcode could provide a 'like' on a topic on Facebook®, or a 'Retweet' on a topic running on Twitter®. Also, it may be used to provide additional information on topics from the radio talk show or newscast that were not covered during the conversation, but that may be available as additional content by scanning the barcode and having access via the mobile device for further review. Accordingly, the present invention contemplates transferring and storing songs, videos, etc via the barcode.

The above can also benefit from a wireless sync to a person(s) mobile device, where the radio display interface would be configured to allow a user to press a button that would link the user's feedback directly to a social media site as described above. Also, if there was additional content for review by the content provider, the user could be prompted to press a button on the radio device interface that would send a link (wirelessly) to the person's mobile device that would allow them to review the content at their leisure.

It should also be appreciated that the radio display device might be completely replaced by the user's mobile device, where the mobile device would have the capabilities of performing the duties of the radio device. In one embodiment, it can be assumed that all functionality would be easily consolidated into a single device the user might carry on their person, allow for even more access to content as technology advances in the mobile device markets For example, a person might use their mobile device as their radio device. This would allow for the content from the radio station displayed on their mobile device (song info, advertisement, etc) allowing the user to benefit from interacting with the content directly on their mobile device. The interaction, feedback, and reporting ability of the invention could all be handled by the mobile device since it could be in two way communications with the radio station whereas the radio device is only receiving data and not pushing data.

It should be appreciated that the present invention may also be used in relation to venues like concerts or bars and clubs where music is being played. For example, in one embodiment patrons might be able to scan a projected image of a barcode that is displayed via a projector where the barcode would be information about the song or a link purchase or download the song. The music/DJ system would be able to output a digital signal that would be converted to the name and artist of the song, or perhaps specific info for a website where a DJ where music mixes might be available for download via a mobile device or computer with an internet connection.

It should be appreciated that data that can be communicated via barcode (or any data send method for that matter) can be applied to the field of social gaming. For instance, the online game Farmville offers an online gaming social community that provides people the ability to interact with virtual avatars/items/environments they have created. When the users take part in 'missions' their virtual avatars expend energy. Thus, the invention provides a novel data input that is generated from the real world and that can be used to 're-energize' the virtual avatarso the player can keep playing. The present invention contemplates a unique type of virtual social environment (such as "Muscleville"), where the data is related to the users building and maintenance of their own bodies and/or fitness center. In this environment, a user can compete against other users in the virtual world by using the exercise/health data they generate and upload into their virtual game account. For example, a user might sign up for a virtual body building competition that is using data responsive to their physical condition. In this case, data that is based on the level of physical activity the user performs in a real world fitness center or other environment, their personalized avatar may apply this data resulting in a modified version (obese, heavy, thin frame, athletic, muscular, etc) of the avatar. Thus, users can earn medals, real or virtual currency rewards, sponsor and other coupons, social status, etc for participating in the many games that can be created and administered. Users might also be able to 'gift' their real world earned/captured data to users in their friends list to help the other user meet a virtual fitness goal (peer motivation). It is contemplated that in one embodiment the state of the fitness center can also be linked to the performance of a person's overall health and activity data. As a user's health/activity levels change (i.e. decrease or increase), the virtual fitness center might have issues with its virtual staff moral, operational capability, equipment problems, cleanliness issues, or virtual default issues that might signify loss of gym membership levels meaning a facility closure is coming near. Thus, the responsibility for the upkeep, employee morale, financial success, machine upkeep, and cleanliness of the fitness center all fall upon the performance of the user in the real world.

It should be appreciated that the present invention as related to dietary tracking can also be applied to the social gaming environment. This would provide an additional data input set that can be used to modify the attributes of the game play (health of the avatar, currencies/pts/XP rewarded to player based on weekly results of food purchased that are related to the real world condition of the player and how much calorie intake they are consuming). The player's food purchases might also affect the virtual physical shape of the user and/or the type of virtual food/drink options that become available to the 'gym members' of the players virtual fitness center. For example, if a player is using the scanning system in the real world to capture data on their dietary intake, the total nutritional value of the food items scanned can be used to generate a virtual equivalent of what is available to the gym members in the fitness center. This may help the player in the real world make more healthy eating choices since the player wants to keep playing the game and keep his fitness center and gym members healthy. Also by not using the barcode system for tracking the dietary data, the user might end up starving his virtual gym members. It should be appreciated that any type of exercise/health data may be applied to this embodiment as well as data coming from various sources, such as personal wearable devices, exercise equipment, mobile devices, health kiosks with biological monitoring abilities, personal mobile health devices (glucometers), data from video game console systems using exercise tracking or motion control technology, etc.

Accordingly, the present invention can be used to teach the user how to stick to a diet regime and eat healthy (or healthier) for their particular physical condition and may be integrated with existing dieting systems, such as Weightwatchers®, Nutrisystem®, etc. to help motivate and keep track of their customers and members. Moreover, the present invention may be used by insurance companies for various reasons, such as to keep track of customers, or establish rates, etc.

In still yet another embodiment, the invention may be applied to the automotive industry to aid a user in adhering to prescribed maintenance procedures, tracking of service history on vehicle, understanding the warning lights/symbols (i.e. 'check engine light'), part replacement warning (muffler, brakes, etc) and how consumers can get preemptive real time up to date information on how much a repair might cost. A hardware device that is communicating with a vehicle's computer system can generate a barcode that has the On-Board-Diagnostics information. When this data is scanned by a mobile device, a person may receive information discounts for local service providers based on their GPS co-oridinates provided by the mobile device. This might allow the person the ability to remotely schedule an appointment for the repair service from the selected discount provider specific to the error code that was detected by scanning the barcode. The person might also receive a recall notification based on the results of scanning the barcode. This allows car manufactures to monitor in field repair statistics and measure efficiency of car components being serviced or replaced by make or model. The barcode generation device may have the ability to capture data on all fluid levels, tire pressure, etc and perform self assessments for emissions. The barcode would be scanned and the mobile device might send data to state DMV websites allowing the user and DMV to save time and money compared to the current process and can also identify vehicles that are not running in a safe emission zone more readily since users can capture data more frequently using mobile devices.

The system can also capture information on speed data that might be able to help prove how fast a person was going moments before an accident (internally memory can store hours and hours of data), where this data can also be shared with car insurance providers on a monthly basis as part of an incentive program for reduced premiums based on safe speed levels. A vehicle might have sensors that detect cigarette/cigar smoke and can report if a person was smoking inside the car (applicable to rental car companies where they could charge an added fee if people smoke when they aren't supposed to), this could also be applied to detected various drugs as well (weed, crack, etc).

In still yet another embodiment, the present invention may have application in fields involving industrial/commercial equipment.

In still yet another embodiment, the present invention may include augmented reality codes that can be used to simplify the user interface of a machine. For example, a consumer fitness exercise machine might have a code that can be scanned by a mobile device. When the mobile device scans the code, a virtual user interface can be generated specific to the operation of the exercise machine. The advantageously allows equipment manufacturers to focus on simplifying and reducing their cost of manufacturing by creating equipment that can simply plug into the mobile device. The mobile device's virtually generated user interface can be configured to control all operation of the exercise machine and can be used with any type of exercise machine (strength, cardio, cables, etc). The mobile devices interface (iPad® or other Tablet® PC's for example) can also be customized by the user. This might allow them to share or bring their mobile device to other places where compatible fitness equipment can support this augmented reality custom generated interface. This augmented reality user interface can be useful for allowing the equipment provider to constantly keep their look and feel as well as software updated with the latest and greatest user interface technologies. Since the mobile device can be networked independent of the exercise machine, this allow for seamless content management and on the fly updates and improvements that can be seamless to the user. This interface can also be perfect for sharing data out of the exercise machine since the display could be configured to generate barcodes as described herein.

Accordingly, one embodiment of the invention includes the generation of barcodes and exercise equipment (and associated display hardware) that display the barcodes via an electronic display, where the barcode includes desired information (inside the barcode image), such as, exercise performance data from the exercise machine and/or from other sensors worn on the person, exercise machine performance data (error codes, serial number, software info, make/model, utilization info, etc), advertising information from content that was displayed during the exercise session, specific channel information as to what channel(s) the user was watching during the session and for how long each channel was on, coupons or other messaging info that was displayed to the user allowing them to purchase or redeem data when scanned on their mobile device, value points (a metric that was outputted from the exercise machine based on performance of session or other factors), URLs used for pointing data to a web server or used for authenticating data set for a mobile device application, and other unique aspects (such as digital dynamic barcode generation component can allow for the size of the barcode to change based on the amount and types of data that are used to create the barcode). It is contemplated that the barcode can also include a combination of colors to further enhance the amount of data capture (reference the HCCP barcode type).

Additionally, another embodiment of the invention includes a content/media delivery and display system that allows a user to scan the media that is displayed to them. The scannable media can be a barcode or any image or media type that allows a user's mobile device to scan and create interaction with the media on their mobile device (such as smart phone). It should be appreciated that the scannable media can be delivered to the exercise machine wirelessly and be displayed on the machine or any aftermarket display, the media can be triggered for display based on the performance of the workout session (example: burn 300 calories and a specific image file is displayed to the user when they hit that milestone) and/or the media can contain static QR code links that allow the user to have a transactional capability with the system as part of their workout (they can purchase products, claim coupons, purchase services from the venue, claim points, etc). When scanned with a mobile device, the system can use augmented reality techniques to present dynamic content on the user's mobile device, allowing the user to interact with the AR content on their mobile device. This allows the static media content to now become interactive, further promoting a transactional capability. Moreover, the system can allow a user to authenticate themselves on the system by scanning the media which can be linked to a specific machine (example: a barcode that has a wifi MAC address linked to the display electronics of the machine), or also by wirelessly communicating with the machine with their mobile device as a way to authenticate their presence on the machine. This allows more specific content related to a profile of the user to be displayed during their workout session. Furthermore, the system can also provide a method of rewarding the user for interacting with the scannable media. For example, when the user interacts or scans the media with their mobile device, they can earn points, rewards, etc on the system. The scannable media can be delivered to the user not only at the exercise machine, but also on digital signage and printed media that would be found in the venue.

In still yet another embodiment, the system may enables medical devices to have similar data capture capabilities, where a device like a blood glucose meter can display a digital barcode (QR code) that has information related to the test results of the user. For example, the digital barcode display can have an embedded URL that allows ANY mobile device scanning application to be able to send the data to a predetermined web server (this requires no need for any mobile application development). Moreover, multiple test results can be inside the dynamic QR code display. Data such as number of test strips consumed can also be provided and this data can also power a QR code image that allows the system to provide consumption information on test supplies that can be used to help accurately fulfill the next batch of test supplies for the user, thus eliminating cost out of current test supply fulfillment systems. Furthermore, an aftermarket module can plug into the medical device (or communicate wirelessly) requesting data from onboard memory of the medical device. This module may process and also have display capabilities for generating a QR code for scanning. It should be appreciated that this can also be applied to any type medical device such as DNA sequencers, hemotology equipment, etc allowing test results to be easily captured on mobile device (included machine performance data characteristics as well for machine diagnostics).

Additionally, other embodiments contemplate that the exercise machine might have scannable media (either printed or digitally displayed) that would allow a user to interact with the media with their mobile device allowing for instructions on how to use the machine or provide information on programming information that the machine has. The mobile device may be able to display this information through a website viewable on the mobile device or through augmented reality content that is display on the mobile device through interaction with the scannable media. For example, one use may include a grocery store system that would allow a user to scan nutritional information from a display or even a receipt that has a barcode that contains a summary of all of the nutrition information on the food products they had just purchased. This data can be shared into any software application that would be able to apply the data as part of a prescribed nutrition program specific to the user. Another use may include a payment system that allows a user to scan a barcode display on a machine that has information specific to a purchase of a product or service. The mobile device would be connected online to a server so when the user scans the machine interface (example: Red Box), where the user's payment information would come from their mobile device and then the server would communicate with the machine completing the transaction.

Still yet another embodiment may include a system for interacting with audio devices (such as, a car or portable radio) where content such as music, advertisements, coupons, etc, can be contained in a digital QR code displayed on the audio device allowing the user to gain access to content that is typically not delivered to the user when music is playing. Thus, this allows for content to be delivered to a user listening to a audio device where the content is generated in scannable format for the user. Moreover, the user could also interact with the audio device display to provide feedback or trigger other actions such as purchases, where the content is sent wirelessly to their mobile device. This would allow the radio station to have feedback on the content their users are listening to as well as provide a ranking system for content that is powered in real time by the users. The mobile device would be connected via a software application that would receive the content from the audio device and then also be connected to a webserver that is hosted by the radio station content system. This provides a full feedback system for the radio station and also allows them to sell a new type of advertisement inventory to companies since they can know benefit from ads sent to a user while music is being played.

In still yet another embodiment, a system for controlling a machine (treadmill, car radio, etc) where sensors are used to optically detect parameters of a person during use of the machine is provided. The sensor (xBox® Kinect® for example) may be in communication with the machine allowing for the system to detect heat signatures of the person during a workout non-volitionally, hand gestures, etc. This sensor configuration would allow the user to control the machine characteristics by not having to press a display control button on the machine. The sensor could also use hand gestures by the user to control the volume of a TV, channel, speed, incline, etc. The sensor can also detect the profile of the user (age, gender, weight, etc) and use this information to set the controls of the machine and use the data to better predict calorie expenditure. The sensor configuration can fully integrated into the machine, part of an TV display attached to the machine, or part of a smart phone (or other device) that is in communication with the machine.

In still yet another embodiment, a system for using facial recognition during an exercise session is provided, where the sensor technology can detect when a user is looking at a video display screen (on the treadmill or aftermarket TV), and where the sensor is able to report how frequently a user is looking at the screen. This can allow the system to report on when a user is looking at a screen that might have advertising content display, allowing the system to verify the effectiveness of the content and report the amount of time the user is spending looking at the screen during a workout session. This sensor technology may also be able to identify the profile of the user, and would further allow the system to send more relevant content to the user for display while the workout since this information can be used by a content management system to filter less relevant content. The sensor can also be used to authenticate a user that might allow the machine to turn on if they are authenticated as being allowed to use that specific machine based on payment status for access to the facility or even having a valid membership.

In accordance with an exemplary embodiment, the invention may be implemented through a controller operating in response to a computer program. In order to perform the prescribed functions and desired processing, as well as the computations therefore (e.g. execution control algorithm(s), the control processes prescribed herein, and the like), the controller may includes, but not be limited to, a processor(s), computer(s), memory, storage, register(s), timing, interrupt(s), communication interface(s), and input/output signal interface(s), as well as combination comprising at least one of the foregoing. Moreover, the invention may be embodied in the form of a computer or controller implemented processes.

The methods and embodiments of the invention described herein and illustrated in the several figures may be embodied in the form of computer-implemented processes and apparatuses for practicing those processes. As such, the methods and embodiments described hereinabove and in the several figures may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention.

The methods and embodiments described hereinabove and in the several figures may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention.

It should be further appreciated that the methods and embodiments described hereinabove may also be practiced, in whole or in part, via any device suitable to the desired end purpose, such as a computer, iPod, MP3 Player, a PDA, a Pocket PC, Tablet PC, Smartphone and/or a Cell phone with connection capability.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another. An apparatus and method for processing exercise information is provided, wherein the method includes obtaining exercise information, processing exercise information responsive to predetermined goals to generate resultant information and displaying the resultant information.

What is claimed is:

1. A wearable activity device, wherein the wearable activity device is comprised of:
   a display device;
   at least one of an accelerometer configured to track activity and an embedded bio-metric monitoring sensor configured to detect a bio-metric characteristic;
   wireless communication circuitry, wherein the wireless communication circuitry is configured to establish a wireless communications link with a mobile device;
   at least one processor with software, wherein the processor is associated with a memory device and wherein the at least one processor is in signal communication with the display device and the wireless communication circuitry;
   the memory device associated with the at least one processor, wherein the memory device is configured to store wireless pairing information associated with the wireless communication circuitry;
   wherein the processor software is configured to;
      obtain, from the memory device, the wireless pairing information associated with the wireless communication circuitry,
      generate a color coded digital scannable media responsive to the wireless pairing information,
      control the display device, wherein the display device is configured to display the color coded digital scannable media,
      establish, via the wireless communication circuitry, the wireless communications link with the mobile device responsive to the mobile device scanning and decoding the color coded displayed digital scannable media,
      generate at least one of activity tracking information and bio-metric information, and
      communicate, via the wireless communications link, at least one of the activity tracking information and the bio-metric information to the mobile device.

2. The wearable activity device of claim 1, wherein the wearable activity device is at least one of a smartwatch device and a wearable health monitoring device.

3. The wearable activity device of claim 1, wherein the wireless communication circuitry is further configured to establish at least one of a near field communications link, a wide area network communications link, and a personal area network communications link with the mobile device.

4. The wearable activity device of claim 1, wherein the mobile device is at least one of a smartphone and a tablet device.

5. The wearable activity device of claim 1, wherein the wireless pairing information associated with the wireless communication circuitry is at least one of a MAC address identifier associated with the wireless communication circuitry and an identification identifier associated with the wearable activity device.

6. The wearable activity device of claim 1, wherein the wireless pairing information is encrypted by the processor software.

7. The wearable activity device of claim 1, wherein the wireless pairing information further includes a combination of the wireless communication circuitry information and at least one of user identification identifier and wearable activity device information.

8. The wearable activity device of claim 7, wherein the wearable activity device information is at least one of the wearable activity device type, an error code associated with the wearable activity device, workout performance data generated by the wearable activity device, date and time stamp information generated by the wearable activity device, facility location identifier associated with the physical location of the wearable activity device, user ID information associated with a user of the wearable activity device, wearable activity device software information, and wearable activity device utilization information.

9. The wearable activity device of claim 1, wherein the color coded digital scannable media includes at least one of a QR code, a 2D Matrix code, a 3D barcode, a representation of non-human readable information using colored pixels, an augmented reality marker, an augmented reality image, and an augmented reality code.

10. The wearable activity device of claim 1, wherein the display device is at least one of a touchscreen display, a LED display and a LCD display.

11. A method for establishing a communications link between a wearable activity device and a mobile device, the method comprising:
   storing, by a memory device associated with the wearable activity device, wireless pairing information associated with wireless communication circuitry disposed within the wearable activity device,
   receiving, by a processor associated with the wearable activity device, the wireless pairing information associated with the wireless communication circuitry from the memory device,
   generating, by the processor associated with the wearable activity device, a color coded digital scannable media responsive to the wireless pairing information,
   displaying, by a display device associated with the wearable activity device, the color coded digital scannable media,
   scanning, by the mobile device, the color coded digital scannable media,
   processing, by the mobile device, the color coded digital scannable media, and establishing, by the mobile device, a wireless communications link with the wearable activity device responsive to the mobile device processing the color coded digital scannable media, generating, by the wearable activity device processor, at least one of activity information and bio-metric information, wherein the at least one of the activity information and bio-metric information is stored in the memory device associated with the wearable activity device, and communicating, via the wireless communications link by the wearable activity device, at least one of the activity tracking information and the bio-metric information to the mobile device.

12. The method of claim 11, wherein the wearable activity device is at least one of a smartwatch device and a wearable health monitoring device.

13. The method of claim 11, wherein the wireless communication circuitry is further configured to establish at least one of a near field communications link, a wide area network communications link, and a personal area network communications link with the mobile device.

14. The method of claim 11, wherein the mobile device is at least one of a smartphone and a tablet device.

15. The method of claim 11, wherein the wireless pairing information associated with the wireless communication circuitry is at least one of a MAC address identifier associated with the wireless communication circuitry and a wearable activity device identification number associated with the wearable activity device.

16. The method of claim 11, wherein the wireless pairing information is encrypted by the wearable activity device processor software.

17. The method of claim 11, wherein the wireless pairing information further includes a combination of at least one of a user identification identifier, the wireless communication circuitry information and the wearable activity device information.

18. The method claim 17, wherein the wearable activity device information is at least one of the wearable activity device type, an error code associated with the wearable activity device, workout performance data generated by the wearable activity device, date and time stamp information generated by the wearable activity device, facility location identifier associated with the physical location of the wearable activity device, user ID information associated with a user of the wearable activity device, wearable activity device software information, and wearable activity device utilization information.

19. The method of claim 11, wherein the digital scannable media is at least one of a QR code, a 2D Matrix code, a 3D barcode, a representation of non-human readable information using colored pixels, a augmented reality marker, a augmented reality image, and a augmented reality code.

20. The method of claim 11, wherein the display device is at least one of a touchscreen display, a LED display and a LCD display.

* * * * *

UNITED STATES PATENT AND TRADEMARK OFFICE
CERTIFICATE OF CORRECTION

| | | |
|---|---|---|
| PATENT NO. | : 11,664,123 B2 | |
| APPLICATION NO. | : 17/181423 | |
| DATED | : May 30, 2023 | |
| INVENTOR(S) | : Sean McKirdy | |

It is certified that error appears in the above-identified patent and that said Letters Patent is hereby corrected as shown below:

On the Title Page

Item (63) under "Related U.S. Application Data" delete the paragraph and insert the following:
-- Continuation of application No. 16/412,585, filed on May 15, 2019, now Pat. No. 10,926,135, which is a continuation of application No. 15/175,599, filed on Jun. 6, 2016, now Pat. No. 10,322,313, which is a continuation of application No. 13/567,337, filed on Aug. 6, 2012, now Pat. No. 9,367,860.
--

Under Related U.S. Application Data, beneath the above inserted paragraph, insert the following:
-- (60) Provisional application No. 61/515,728, filed on Aug. 5, 2011,
Provisional application No. 61/539,587, filed on Sept. 27, 2011, and
Provisional application No. 61/622,175, filed on Apr. 10, 2012. --

In the Specification

Column 1, Line 8, (Paragraph under the section titled: "CROSS-REFERENCE TO RELATED PATENT APPLICATIONS) cancel the text beginning with "The present application ..." and ending "... by reference in their entireties" in Column 1, Line 23, and insert the following replacement Paragraph:
-- The present application is a continuation application of copending U.S. Non-Provisional Patent Application Ser. No. 16/412,585, filed May 15, 2019 (now U.S. Patent 10,926,135, issued on February 23, 2021),
wherein U.S. Non-Provisional Patent Application Ser. No. 16/412,585 claims the benefit of copending U.S. Non-Provisional Patent Application Ser. No. 15/175,599, filed Jun. 6, 2016 (now U.S. Patent 10,322,313, issued on Jun. 19, 2019),
wherein U.S. Non-Provisional patent application Ser. No. 15/175,599 claims the benefit of copending U.S. Non-Provisional Patent Application Ser. No. 13/567,337, filed Aug. 6, 2012 (now U.S. Patent 9,367,860, issued on Jun. 14, 2016),
wherein U.S. Non-Provisional Patent Application Ser. No. 13/567,337 claims the benefit of each of: copending U.S. Provisional Patent Application Ser. No. 61/515,728, filed on Aug. 5, 2011, Signed and Sealed this
Thirteenth Day of August, 2024

*Katherine Kelly Vidal*

Katherine Kelly Vidal
*Director of the United States Patent and Trademark Office* copending U.S. Provisional Patent Application Ser. No. 61/539,587, filed on Sep. 27, 2011, and copending U.S. Provisional Patent Application Ser. No. 61/622,175, filed on Apr. 10, 2012, the contents of all of which are incorporated herein by reference in their entireties. --